(12) United States Patent
Rolfes et al.

(10) Patent No.: US 6,221,399 B1
(45) Date of Patent: Apr. 24, 2001

(54) METHOD OF MAKING CONTROLLED RELEASE PARTICLES OF COMPLEXED POLYMERS

(75) Inventors: Heidi Rolfes, Pretoria; Thilo Lothar Van Der Merwe, Brakpan; Patricia-Ann Truter, Elardus Park, all of (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 09/011,934

(22) PCT Filed: Aug. 16, 1996

(86) PCT No.: PCT/GB96/02016

§ 371 Date: Jun. 1, 1998

§ 102(e) Date: Jun. 1, 1998

(87) PCT Pub. No.: WO97/06787

PCT Pub. Date: Feb. 27, 1997

(30) Foreign Application Priority Data

Aug. 17, 1995 (ZA) .................................................. 95/6870

(51) Int. Cl.[7] .................................. A61K 9/14; C08J 3/12
(52) U.S. Cl. ........................... 424/489; 424/499; 424/500; 424/501; 264/5

(58) Field of Search .................................. 424/484–488, 424/499–501, 489; 264/5, 13; 428/402

(56) References Cited

U.S. PATENT DOCUMENTS 5,202,159 * 4/1993 Chen et al. .

FOREIGN PATENT DOCUMENTS

267788 * 5/1988 (EP) .

* cited by examiner

Primary Examiner—Edward J. Webman
(74) Attorney, Agent, or Firm—Pillsbury Winthrop LLP

(57) ABSTRACT

A method of making a solid interpolymer for use as a controlled release matrix for a controlled release product for oral administration, involves dissolving a first polymer in a solvent therefor, dissolving one or more second complementary polymers capable of complexing with the first polymer to form the interpolymer complex, in a solvent therefor, adding a complexation inhibitor, mixing together the solutions, adjusting the pH if necessary, and spraying the product into a vessel to remove at least partially the solvents and thereby to produce solid particles of the interpolymer complex. An active agent such as a drug is preferably embedded or encapsulated in the interpolymer complex before spray drying or may be incorporated by suitable means at a later stage.

15 Claims, 12 Drawing Sheets

Dissolution Curve for Indomethacin: Release System TP50
PVA 107: PEO N10 (1:1)
Drug: Binder (0.9704), 10mm, 45cam Dissolution Curve for Diltiazem: Release System TP70
PAA K752: HEC 250HX (1:1)
Drug: Binder (0.9704), 10mm, 45cam Dissolution Curve for Verapamil: Release System TP120
Carbopol 971: PVP/PVAc VA64: Gum Arabic (1:1:1)
Drug: Binder (0.9704)

Dissolution Curve for Verapamil: Release System TP121/142
Gantrez S-97: PVP/PVAc VA64: Gum Arabic (1:1:1)
Drug: Binder (0.9116), 240mg Verapamil Dissolution Curve for Verapamil:Release System TP123
Carbopol 907:PVP/PVAc VA64:Gum Arabic (1:1:1)
Drug:Binder (0.9704)

Dissolution Curve for Verapamil:Release System TP240
Gantrez S-97:PVP/VAc VA64 (70:30)
Drug:Binder (0.7874), 12.5mm, 40cam, 2hours pH=1.2 then pH=6
10% sodium starch glycolate Dissolution Curve for Verapamil:Release System TP267
Sodium Alginate LF10/60:PVP/VAc VA64:HPMC E-5 (1:1:1)
Drug:Binder (0.8657), 12.5mm, 40cam, 50rpm
Simulated = 2 hours pH=1.2 then pH=6

Dissolution Curve for Verapamil:Release System TP283
Eudragit L100:HPMC E-5 (1:9)
Drug:Binder (1.5126), 50rpm, 12.5mm, 40cam Dissolution Curve for Diclofenac: Release System TP162
Carbopol 907:PVP/VAc VA64:HPC 99EF (1:1:1)
Drug:Binder (1.3535), drug preprotonated Dissolution Curve for Diclofenac: Release System TP316
Eudragit L100:PVP/VAc VA64:HPMC E-5 (5:65:30)
Drug:Binder (0.926), drug preprotonated
2 hours pH=1.2 then pH=6.8, 8mm, 40cam Dissolution Curve for Diclofenac: Release System TP282
Sodium Alginate LF10/60:PVP/VAc VA64:HPMC E-5(1:1:1)
Drug:Binder (1.2665), drug preprotonated
2 hours pH=1.2 then pH=6.8, 8mm, 40cam Dissolution Curve for Verapamil: Release System TP21/22
PVP K90:PEO N10:PAA K752 (1:1:1)
Drug:Binder (0.9704)

Dissolution Curve for Verapamil: Release System TP13
Gantrez S-97: PVP/VAc E335 (30:70)
Drug: Binder (0.9704), 10mm, 45cam Dissolution Curve for Verapamil: Release System TP40
Gantrez S-97: PVP/VAc E735 (1:1)
Drug: Binder (0.9704), 10mm, 45cam Dissolution Curve for Verapamil: Release System TP43
PAA K752:HEC 250HX (1:1)
Drug:Binder (0.9704), 10mm, 45cam Dissolution Curve for Verapamil: Release System TP45
Gantrez S-97: PVP/VAc E635: Gum Arabic (1:1:1)
Drug:Binder (0.9704)

Dissolution Curve for Indomethacin: Release System TP49
Gantrez S-97:HPC 99LF (1:1)
Drug:Binder (0.9704), 10mm, 45cam Dissolution Curve for Diclofenac: Release System TP60
PAA K752:HEC 250HX (1:1)
Drug:Binder (0.9704), 10mm, 45cam Dissolution Curve for Diclofenac: Release System TP66
Gantrez S-97: NaCMC C30 (1:1)
Drug:Binder (0.9704), 10mm, 45cam Dissolution Curve for Diltiazem: Release System TP73
PVA 107: PEO N10 (1:1)
Drug:Binder (0.9704), 10mm, 45cam Dissolution Curve for Diltiazem: Release System TP76
PAA K752:PEO N10:HEC 250HX(1:1:1)
Drug:Binder(0.9704),10mm,45cam Dissolution Curve for Diclofenac: Release System TP343
Eudragit L100-55:PVP/VAc VA64:HPMC E-5(1:1:1)
Drug:Binder(0.9388), drug preprotonated
2 hours pH=1.2 then pH = 6.8, 8mm, 40cam

METHOD OF MAKING CONTROLLED RELEASE PARTICLES OF COMPLEXED POLYMERS

This application is the national phase of international application PCT/GB96/02016 filed Aug. 16, 1996 which designated the U.S.

BACKGROUND OF THE INVENTION

This invention relates to a method of making a controlled release product from an interpolymer complex and an active agent, to a controlled release product comprising an interpolymer complex having an active agent embedded therein, and to the use of an interpolymer complex as a controlled release matrix for an active agent.

The formation of physical polymer networks by interpolymer complexation is well known [see E Tsuchida & K Abe. Interactions between Macromolecules in Solution and Intermacromolecular Complexes, Springer-Verlag, New York, 1982 and E Tsuchida in *J.M.S.—Pure Appl. Chem.* A31(1) (1994) 1–15]. Interpolymer complexes have been used in medical applications such as permeable contact lenses, permeable wound dressings, corneal implants, vascular grafts, coatings for prosthetic devices, membranes and components for artificial kidneys and blood oxygenators [M K Vogel, R A Cross & H J Bixier *J. Macromol. Sci. Chem.* A4(3) (1970) 675–692].

As discussed by Scranton et al [Polyelectrolyte Gels. Properties. Preparations and Applications, ACS Symposium Series 480, 1992], interpolymer complexes are formed by the association of two or more complementary polymers, and may arise from electrostatic forces, hydrophobic interactions, hydrogen bonding, van der Waals forces or combinations of these interactions. Due to the long-chain structure of the polymers, once a pair of complementary repeating units associate to form a segmental complex, many other units may readily associate without a significant loss of translational degrees of freedom. Therefore the complexation process is cooperative, and stable interpolymer complexes may form even if the segmental interaction energy is relatively small. The formation of complexes may strongly affect the solubility, rheology, conductivity and turbidity of polymer solutions. Similarly, the mechanical properties, permeability and electrical conductivity of the polymeric systems may be greatly affected by complexation.

Tanaka [Polyelectrolyte Gels, Properties, Preparation and Applications, ACS Symposium Series, 1992] classified the assemblies in biological systems into four fundamental attractive interactions, namely: Electrostatic attraction, Hydrogen bonding, Hydrophobic interaction and van der Waals interaction.

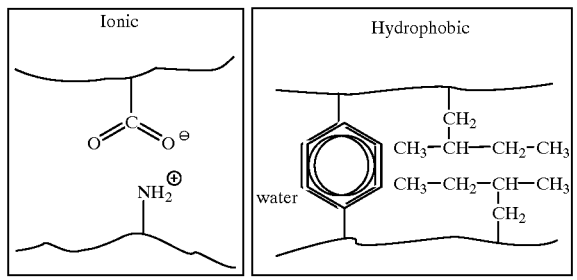

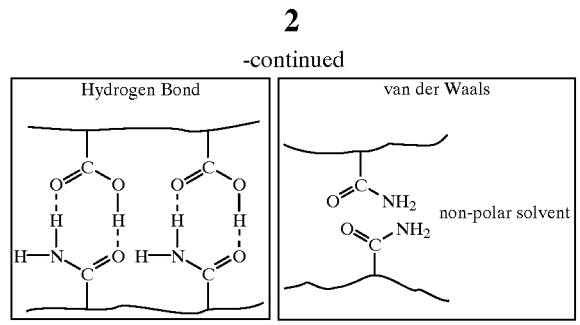

We have shown previously [SA patent 93/4104] how two water-soluble polymers may be converted into a water-insoluble interpolymer complex (at~neutral pH) with a specific molecular/aggregate assembly by purely mixing them in the presence of specific solvents. Unlike covalent polymer networks, interpolymer complexes are solvent reversible. Table 1 illustrates the latter in terms of aqueous solubility.

TABLE 1

Solubility of interpolymer complexes (Adapted from Tsuchida)

| Interpolymer complex | Solubility in aqueous media |
| --- | --- |
| Polyelecrolyte complex | |
| Strong polyacid-Strong polybase | Not soluble in water (soluble in specific ternary solvents) |
| Strong polyacid-Weak polybase | High pH |
| Weak polyacid-Strong polybase | Low pH |
| Weak polyacid-Weak polybase | High and Low pH |
| Hydrogen-bonding complex | High pH. DMSO |

Kono et al [*J. Appl. Pol. Sci.* 59 (1996) 687–693] showed that the permeability of a weak polyacid-weak polybase polyelectrolyte membrane follows similar behaviour to that of solubility as shown in Table 1, i.e., high permeability at low and high pH.

Interpolymer complexes between chitosan and pectin or gum acacia have been applied to controlled release by Meshali et al [*Int. J. Phar.* 89 (1993) 177–181]. They prepared the interpolymer complexes in solution, separated the precipitate from the solution and dried it in an oven. They concluded that the physical mixture of the polymers as opposed to the interpolymer complex, displayed the most efficient sustained release.

Interpolymer complexes are characterized by valuable properties, namely: biological compatibility, hemocompatibility and low toxicity [A V Kharenko & V A Kemenova *Proceed. Intern. Symp. Control. Rel. Bioact. Mater.* 22 (1995) 232–233]. Kharenko et al prepared interpolymer complexes from poly(methacrylic acid) and poly(ethylene glycol) and evaluated their use as a matrix for oral controlled-release formulations, particularly for theophylline. It is stated that the interpolymer complex is formed by hydrogen bonding of the carboxylic protons of PMA to the ether oxygens of PEG. No further description of the manufacture of the controlled release system is given.

In Japanese patent 4-312522, a method for the manufacture of a slow release tablet is given. Hydroxypropylmethylcellulose (HPMC) is suspended in hot water. Tannic acid, an acrylic acid-methylmethacrylate-dimethyl aminoethyl methacrylate polymer or a methacrylic acid-acrylic acid ester copolymer is added. The constituent which is obtained by atomization drying is compressed together with the primary medicinal compound. The slow release is achieved by the viscosity of the HPMC and by coating the tablet with a polymer. There is no mention of the formation of an interpolymer complex or embedding of an active agent therein.

Smith et al [*Ind. Eng. Chem.* 51(11) (1959) 1361–1364] showed how complexation inhibitors may be utilized to re-solubilize interpolymer complexes between poly(acrylic acid) and poly(ethylene oxide). They suggested the use of hydrogen bonding solvents amongst others for this purpose as they suggested these would compete for the hydrogen bonding sites of the respective polymers.

Injectable formulations have been prepared from interpolymer complexes which are stabilized in solution by a complex solubilizer [WO 95/35093]. A pharmaceutical composition including a therapeutic agent and a sustained-release delivery vehicle is disclosed. The delivery vehicle comprises a solution of at least one pharmaceutically acceptable polyacid and at least one pharmaceutically water-soluble, non-ionic polymer, the polyacid and non-ionic polymer forming a stable insoluble interpolymer complex in water at acidic pH, in an aqueous solvent including a pharmaceutically acceptable complex solubilizer, the amount of solubilizer being effective to solubilize the insoluble interpolymer complex. The pharmaceutical composition is intended for injection.

Dangprasirt et al [*Drug Dev. & Ind. Pharm.* 21(20) (1995) 2323–2337] disclose that diclofenac sodium controlled release solid dispersions were prepared by spray drying using ethylcellulose, methacrylic acid copolymer (Eudragit), chitosan, hydroxypropyl methylcellulose and carbomer as single carriers and ethylcellulose—chitosan as combined carriers. Among solid dispersions of 3:1 drug:single carrier, the system containing chitosan exhibited the slowest dissolution. Combined carriers of ethylcellulose-chitosan exhibited more dissolution retarding effect than single carrier of ethylcellulose or chitosan.

Herzfeldt et al [*Pharmazeurische Zeitung* 128(29) (1983) 1589–1592] show that some indomethacin-polymer additive-mixtures have been spray dried by a laboratory spray dryer. The spray dried products were investigated as to their technological behaviour and their dissolution rate properties in relation to the source substance. These investigations resulted in an optimised technological behaviour by spray drying indomethacin without additives but also by spray drying in the presence of cationic polyacrylate. The rapid dissolution rate of the source substance is decreased by spray drying indomethacin in mixtures with methylcellulose and cationic polyacrylate. The spray dried products with polyvinylpyrrolidone including the addition of sodium lauryl sulphate consists of nano- and microcapsules. There is no mention of the formation of interpolymer complexes.

A need exists for novel controlled release products for oral administration, where the release of the active agent from the product can be controlled over a range of release rate and profiles and at different pHs, made by methods which differ from the existing methods described above, which methods provide various advantages such as cost reduction and enhancement of up-scaleability of the methods.

SUMMARY OF THE INVENTION

According to a first aspect of the invention there is provided a method of making a solid interpolymer complex which may be used as a controlled release matrix for a controlled release product for oral administration, from a first polymer and one or more second complementary polymers capable of complexing with the first polymer to form the interpolymer complex, wherein one of the first polymer or the second complementary polymer is, a synthetic polymer, which method includes the steps of:

(1) dissolving the first polymer in a solvent therefor;

(2) dissolving the second complementary polymer in a solvent therefor;

(3) if necessary, adding a complexation inhibitor to the solution of step (1) or the solution of step (2);

(4) mixing together the solutions of steps (1) and (2);

(5) if necessary, adjusting the pH of the mixture of step (4); and (6) spraying the product of step (5) into a vessel to remove at least partially the solvents and thereby to produce solid particles of the interpolymer complex.

According to a second aspect of the invention there is provided a solid interpolymer complex for use as a controlled release matrix for a controlled release product for oral administration, which interpolymer complex is made from a first polymer and one or more second complementary polymers capable of complexing with the first polymer to form the interpolymer complex, wherein one of the first polymer or the second complementary polymer is a synthetic polymer, by a method which includes the steps of:

(1) dissolving the first polymer in a solvent therefor;

(2) dissolving the second complementary polymer in a solvent therefor;

(3) if necessary, adding a complexation inhibitor to the solution of step (1) or the solution of step (2);

(4) mixing together the solutions of steps (1) and (2);

(5) if necessary, adjusting the pH of the mixture of step (4); and (6) spraying the product of step (5) into a vessel to remove at least partially the solvents and thereby to produce solid particles of the interpolymer complex.

According to a third aspect of the invention there is provided a process of making a controlled release product for oral administration from a interpolymer complex and an active agent, wherein the interpolymer complex is made from a first polymer and a second complementary polymer capable of complexing with the first polymer to form the interpolymer complex, wherein one of the first polymer or the second complementary polymer is a synthetic polymer, which includes the steps of:

(a) dissolving the first polymer in a solvent therefor;

(b) dissolving the second complementary polymer in a solvent therefor;

(c) if necessary, adding a complexation inhibitor to the solution of step (a) or the solution of step (b);

(d) mixing together the solutions of steps (a) and (b);

(e) if necessary, adjusting the pH of the mixture of step (d);

(f) spraying the product of step (e) into a vessel to remove at least partially the solvents and thereby to produce solid particles of the interpolymer complex; and (g) incorporating the active agent into the interpolymer complex to form the controlled release product.

The process may be carried out in various ways.

Firstly, the process may be carried out by:

(a) dissolving the first polymer in a solvent therefor;

(b) dissolving the second complementary polymer in a solvent therefor;

(c) if necessary, adding a complexation inhibitor to the solution of step (a) or the solution of step (b);

(g) providing the active agent in the form of a dry powder or in the form of a solution, dispersion, suspension, emulsion or slurry of the active agent in a liquid medium; and either (d)(i) mixing the product of step (g) with either the solution of step (a) or the solution of step (b) and then mixing together the solutions of step (a) and step (b); or (d)(ii) mixing together the solutions of step (a) and step (b) and the product of step (g); (e), if necessary, adjusting the pH of the mixture of step (d); and then (f) spraying the product of step (e) into a vessel to remove at least partially the solvents and the liquid medium when present and thereby to produce solid particles of the interpolymer complex with the active agent embedded or encapsulated therein.

Secondly, the process may be carried out by preparing the interpolymer complex as set out above in steps (a) to (f) and then:

(g) mixing the active agent in solid or liquid form with the interpolymer complex, and compressing the product to produce a tablet or a mini tablet.

Thirdly, the process may be carried out by performing steps (a) to (e) above and then:

(f) spraying the product of step (e) into a vessel in which the active agent is being fluidized thereby encapsulating the active agent particles in a coating of the interpolymer complex.

According to a fourth aspect of the invention there is provided a controlled release product for oral administration which comprises a solid interpolymer complex and an active agent incorporated into the interpolymer complex, wherein the interpolymer complex is made from a first polymer and a second complementary polymer capable of complexing with the first polymer to form the interpolymer complex, wherein one of the first polymer or the second complementary polymer is a synthetic polymer, by a method which comprises the steps of:

(1) dissolving the first polymer in a solvent therefor;

(2) dissolving the second complementary polymer in a solvent therefor;

(3) if necessary, adding a complexation inhibitor to the solution of step (1) or the solution of step (2);

(4) mixing together the solutions of steps (1) and (2);

(5) if necessary, adjusting the pH of the mixture of step (4); and (6) spraying the product of step (5) into a vessel to remove at least partially the solvents and thereby to produce solid particles of the interpolymer complex.

According to a fifth aspect of the invention there is provided the use of a solid interpolymer complex formed from a first polymer and a second complementary polymer capable of complexing with the first polymer to form the interpolymer complex, wherein one of the first polymer or the second complementary polymer is a synthetic polymer, by a method which comprises the steps of:

(1) dissolving the first polymer in a solvent therefor;

(2) dissolving the second complementary polymer in a solvent therefor;

(3) if necessary, adding a complexation inhibitor to the solution of step (1) or the solution of step (2);

(4) mixing together the solutions of steps (1) and (2);

(5) if necessary, adjusting the pH of the mixture of step (4); and (6) spraying the product of step (5) into a vessel to remove at least partially the solvents and thereby to produce solid particles of the interpolymer complex;

as a controlled release matrix for a controlled release product for oral administration.

The interpolymer complex may be formed from a first polymer and one or more second complementary polymers, such that the first polymer and the one or more second complementary polymers all interact to form the interpolymer complex.

The solvents used in steps (1) and (2) of the method of the invention, the solvents used in steps (a) and (b) of the process of the invention and the liquid medium used in step (g) of the process of the invention, may consist of single solvents or may be a mixture of solvents or a single liquid medium or may be a mixture of liquid media. Further, the solvents used in steps (1) and (2) and in steps (a) and (b) may be the same or different. The liquid medium of step (g) may be a solvent for one or more of the first or second complementary polymers.

The spraying in step (6) or step (f) may be achieved by spray drying or by spray granulation techniques or the like. Preferably the spraying is spray drying.

A complexation inhibitor must be present to prevent the interpolymer complex from precipitating from solution prior to step (6) or step (f). The solvent or solvents or liquid medium used may be chosen to act as complexation inhibitors. Alternatively, where none of the solvent or solvents or liquid medium is a complexation inhibitor then a complexation inhibitor such as for example acetic acid, ethanol, acetone, DMSO or a hydrogen bonding substance or the like, must be added to the solvent or solvents in steps (1) or (2) or in steps (a) or (b) and optionally also to the liquid medium.

The complexation inhibitors are preferably volatile complexation inhibitors, viz, hydrogen bonding solvents such as ethanol, acetone or the like with relatively low boiling points.

Definitions

The active agent may be a drug for humans or animals, or a food supplement such as a vitamin or a mineral, or the like.

The term polymer may refer to the first polymer or to any one of the second complementary polymers.

The term polymer includes copolymers.

By complexation there is meant reversible physical molecular forces such as hydrogen bonding, hydrophobic interactions, van der Waals forces, electrostatic-, ionic- or Coulomb forces and combinations of these interactions and excludes irreversible chemical forces such as covalent bonding.

The pH of the polymer solution before spray drying determines the interpolymer complex formed and the release rate of active agent from the dosage form and this must be adjusted, if necessary, to give the desired product. For hydrogen bonding interpolymer complexes in which one of the polymers is a polyacid, the preferred pH of the solution prior to spray drying is preferably below the pKa value of the acid groups on the polyacid.

DESCRIPTION OF EMBODIMENTS

Figure 1:
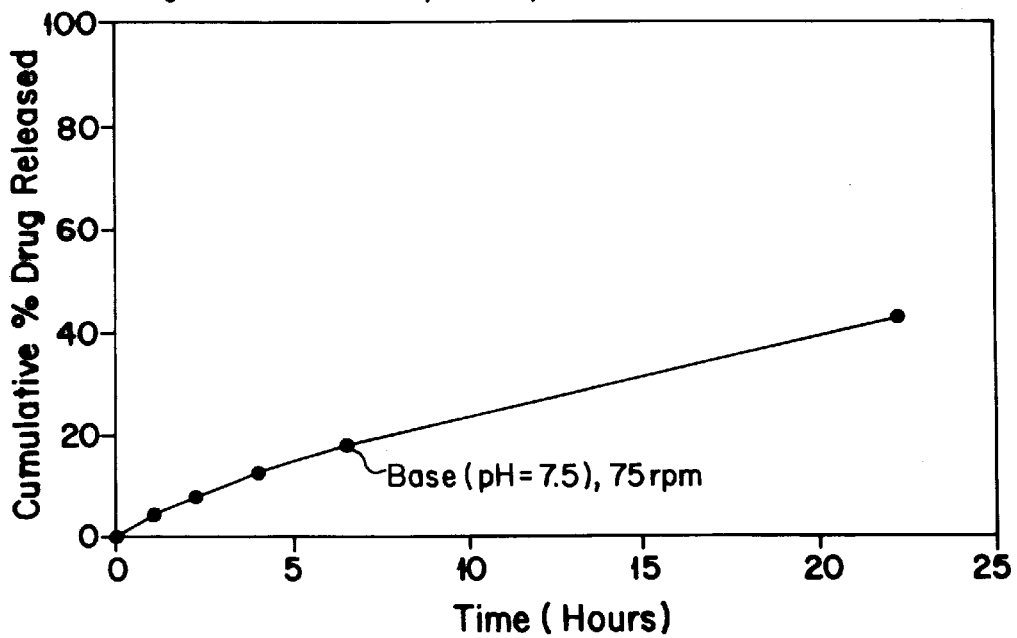
FIGS. 1 to 22 are dissolution graphs of the products of Examples 1 to 22.

According to a first aspect of the invention there is provided a method of making a solid interpolymer complex which may be used as a controlled release matrix for a controlled release product for oral administration, from a first polymer and one or more second complementary polymers capable of complexing with the first polymer to form the interpolymer complex, wherein one of the first polymer or the second complementary polymer is a synthetic polymer, which method includes the steps of:

(1) dissolving the first polymer in a solvent therefor;

(2) dissolving the second complementary polymer in a solvent therefor;

(3) if necessary, adding a complexation inhibitor to the solution of step (1) or the solution of step (2);

(4) mixing together the solutions of steps (1) and (2);

(5) if necessary, adjusting the pH of the mixture of step (4); and (6) spraying the product of step (5) into a vessel to remove at least partially the solvents and thereby to produce solid particles of the interpolymer complex.

This method is the crux of the present invention.

The interpolymer complex made by the method of the invention is intended for use as a controlled release matrix for a controlled release product for oral administration. In this regard, an active agent is incorporated into the interpolymer complex to form the controlled release product.

The incorporation of the active agent into the interpolymer complex may be achieved in various ways including incorporating the active agent into the interpolymer complex as it is formed, so that the active agent is embedded or encapsulated in the interpolymer complex, by coating the active agent particles with the interpolymer complex in a fluidized bed, or by post mixing the interpolymer complex with the active agent and then compressing the result to form a tablet of the interpolymer complex with the active agent incorporated therein.

The controlled release products of the invention may be designed to have a wide range of release rates and profiles, including a substantially zero-order release rate over a period of time between 2 and 72 hours. In addition, the controlled release products of the invention may be either pH insensitive, acid sensitive or base sensitive, pH insensitive products release the active agent at the same rate irrespective of the pH of the surrounding environment; acid sensitive products release the active agent faster in an acidic environment; and, base sensitive products release the active agent faster in a basic environment.

As stated above, the active agent may be a drug for humans or animals, in which case the controlled release product of the invention will be a controlled release pharmaceutical product or a controlled release veterinary product. Alternatively, the active agent may be a food supplement such as a vitamin or a mineral.

Suitable classes of drugs for use in the controlled release product of the invention include:
opioid agonists, opioid antagonists, benzodiazepines, butyrophenones, GABA stimulators, substituted phenols, antiarrhythmics, beta blockers, ACE inhibitors, calcium channel blockers, antihypertensives, antihypertensive/angina drugs, diuretics, angina-acting drugs, antihypertensive/angina/vasodilator-acting drugs, hypotensive-acting drugs, antiemetics, antifungals, antiparkinson drugs, bronchodilators, antimigraine drugs, oxytocic drugs, antidiuretics, antihyoperglycemics, macromolecular drugs, amino acids, polysaccharides, polypeptides, antigens, nucleosides, antibodies, vitamins, enzymes, central nervous system-acting drugs, cardiovascular-acting drugs, renal vascular-acting drugs, anxiolytics, analgesics, anesthetics, antianginals and antibiotics.

Specific examples of suitable drugs are:
nicotine, atropine, scopolamine, ondansetron, sumatriptan, rizatriptan, naratriptan, ketorolac tromethamine, oxybutinin, meclofenamate, piroxicam, ketoprofen, indomethacin, ibuprofen, diclofenac, flurbiprofen, lornoxicam, meloxicam, celecoxib, montelukast, cyclosporin, nimesulide, zidovudine, etoposide, tromadol, morphine, diltiazem, cisapride, omeprazole, fentanyl, alfentanil, sufentanil, lofentanil, carfentanil, naloxone, nalbuphene, diazepam, lorazepam, lormetazepam, midazolam, oxazepam, triazolam, ketamine, levodopa, bretylium, captopril, ramipril, clonidine, dopamine, enalapril, esmolel, furosemide, isosorbide, labetolol, lidocaine, metolazone, metoprolol, nadolol, nifedipine, nicardipine, nitrendipine, nisoldipine, amlodipine, nitroglycerin, nitroprusside, propranolol, benzquinamide, meclizine, cyclizine, metoclopramide, prochlorperazine, trimethobenzamide, clotrimazole, nystatin, carbidopa, verapamil, levodopa, albuterol, aminophylline, beclomethasone, dyphylline, epinephrine, flunisolide, isoproterenol HCl, metaproterenol, oxtriphylline, terbutaline, theophylline, ergsotamine, dihydroergotamine, methysergide, propranolol, atenolol, suloctidil, salmeterol and pentoxiphylline.

Drugs of particular interest are verapamil, diltiazem, indomethacin, diclofenac, isosorbide-5-mononitrate, zidovudine, pentoxiphylline, levodopa/carbidopa and cisapride.

The polymers used to form the interpolymer complex of the invention may be linear, branched, star shaped, comb shaped or cross-linked. Preferably the polymers are linear or combinations of linear and cross-linked hydrophilic polymers or their co-polymers.

At least one of the polymers forming the interpolymer complex must be a synthetic polymer. Synthetic polymers offer the advantages, over naturally occurring polymers, of homogeneity and predictability of properties and chemical composition.

When the interpolymer complex is a hydrogen bonding complex and the first polymer is a polyacid, preferably the pH is such that the polyacid is in its unionized state with no charge, i.e., pH<pKa value of the acid groups, and the second complementary polymer is a polymer with hydrogen bonding sites.

When the interpolymer complex is a polyelectrolyte complex, preferably the first polymer is a strong polyacid and the second complementary polymer is a weak polybase.

Examples of suitable polymers from which the first polymer and the second complementary polymer may be selected are: alginates; alkyl and hydroxyalkylcelluloses; carboxymethylcellulose and its salts; carrageenan; cellulose and its derivatives; guar gum; gum arabic; methyl vinyl ether/maleic anhydride copolymers; pectins; poly (acrylamide); poly(acrylic acid) and its salts; poly(ethylene glycol); poly(ethylene imine); poly(ethylene oxide); poly (methacrylic acid); poly(vinyl acetate); poly(vinyl alcohol); poly(vinyl amine); poly(vinyl) pyrrolidone); poly(vinyl sulphonic acid); starches and their derivatives; styrene/maleic anhydride copolymers; xanthan gum; or the like and their copolymers.

For diclofenac or its sodium salt, the preferred interpolymer complex may be formed from:
methyl methacrylate/methacrylic acid copolymer with vinyl pyrrolidone/vinyl acetate copolymer and with hydroxypropylmethylcellulose, in a preferred mass ratio of 1:1:1, with the mass ratio of drug to interpolymer complex being preferably 1:1; or methylmethacrylate/methacrylic acid copolymer with hydroxypropylmethylcellulose, in a preferred mass ratio of 10:90, with the mass ratio of drug to interpolymer complex being preferably 1:1.

These systems are illustrated in Examples TP 315, TP 317 and TP 343.

For verapamil, the preferred interpolymer complex may be formed from:
methyl methacrylate/methacrylic acid copolymer with hydroxypropylmethylcellulose, in a preferred mass ratio of 10:90, with the mass ratio of drug to interpolymer complex being preferably between 6:4 to 4:6.

These systems are illustrated in Examples TP 283 and TP 310.

The solvents and liquid medium used may be the same or different. Further, each of the first polymer, the second complementary polymer or polymers is dissolved in a mixture of solvents and/or liquid media. The active agent may be dissolved, dispersed, suspended, emulsified or slurried separately in the solvents or liquid medium or may be dissolved, dispersed, suspended, emulsified or slurried together with the polymers in a mixture of solvents and/or liquid media.

Suitable solvents and liquid media include: water; ethanol, propanol and other alcohols; acetone and the like and mixtures thereof.

The solvent or solvents or liquid medium may be chosen to act as complexation inhibitors, to prevent the interpolymer complex from precipitating prior to step (4) or step (d). Alternatively, a complexation inhibitor such as acetic acid or acetone must be added to the solvent or solvents or liquid medium. Generally, hydrogen bonding solvents such as acetone and ethanol are used as complexation inhibitors. Another example of a non volatile complexation inhibitor is glycerine.

The spraying in step (6) or step (f) may be achieved by spray drying, spray coating or spray granulation techniques. Preferably the spraying is spray drying.

The spray drying, spray coating or spray granulation may be carried out using conventional techniques.

For example, suitable parameters for spray drying are as follows:
Inlet temperature—between 60° C. and 180° C., preferably between 120° C. and 140° C.; peristaltic pump speed range—between 60 ml/h and 800 ml/h, resulting in an outlet temperature of between 70° C. and 110° C., preferably between 180 ml/h and 600 ml/h, resulting in an outlet temperature of between 85° C. and 95° C.;
air flow rate—between 200 and 800 Nl/h, preferably between 500 and 600 Nl/h; total concentration of polymer in solution—between 0.1 and 10%, preferably with a solid content between 2 and 5%.

The solid product of step (6) or step (f) may be blended with conventional pharmaceutical excipients such as a glidant (eg silicic acid), a lubricant (eg magnesium stearate), and a disintegrant (eg sodium starch glycolate), according to conventional techniques and in conventional quantities.

In step (g), compression includes conventional compression in a tableting machine as well as extrusion and other techniques where pressure is applied to the mixture of interpolymer complex and active agent.

The result of step (g) above may be a conventional tablet or a mini tablet for incorporation for example into a capsule.

The controlled release product produced by the method of the invention may be used as such or may be pressed into tablets or used in other dosage forms such as capsules. Preferably the controlled release product is pressed into tablets. When the controlled release product of the method of the invention is pressed into tablets, the product may be mixed with suitable amounts of conventional excipients such as disintegrants, e.g., crosslinked poly(vinyl pyrrolidone), microcrystalline cellulose and sodium starch glycolate, and lubricants, e.g., calcium stearate and magnesium stearate.

The invention will now be described in more detail with reference to the following examples and the figures. All the Examples were carried out using a Mini Spray Dryer 190 from Büchi Laboratorium-Technik.

EXAMPLES

Example 1 (TP50)

The following solutions were prepared: (a) 100 g of a 2% solution of poly(vinyl alcohol) in water, (b) 100 g of a 2% solution of poly(ethylene oxide) in a water:ethanol (1:1) mixture. 4 g Indomethacin was added to solution (b), the resulting suspension was mixed with solution (a) and spray dried. The spray dried granules were blended with a lubricant and compressed into a tablet and in vitro dissolution studies were performed as illustrated in FIG. 1.

Example 2 (TP70)

Figure 2:
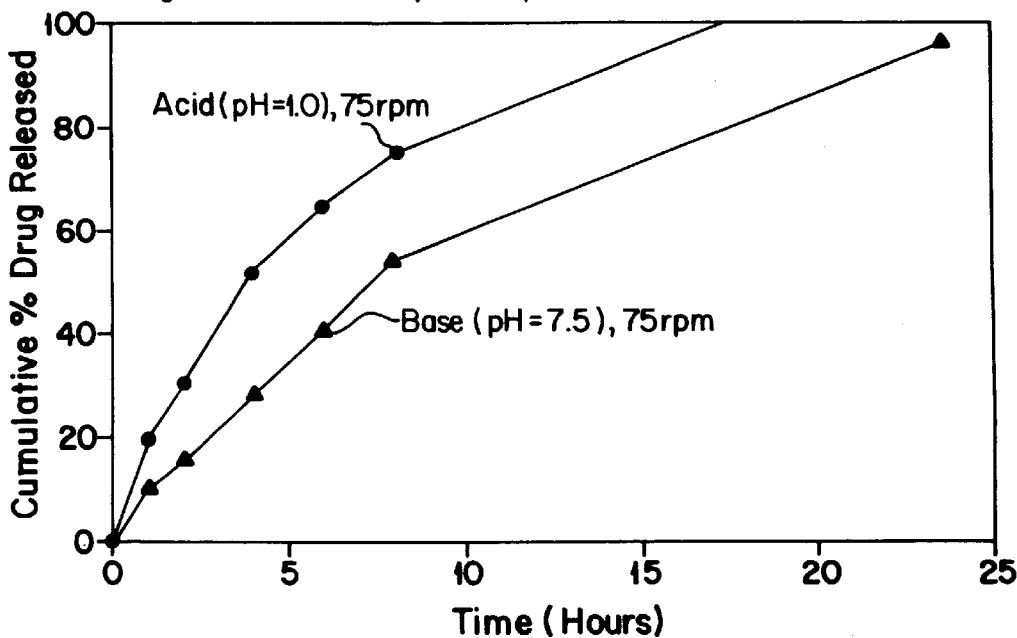

Method as in Example 1 with (a) 100 g of a 2% solution of poly(acrylic acid) in a water:ethanol (1:1) mixture, (b) 100 g of a 2% solution of hydroxyethyl cellulose in water. 4 g Diltiazem hydrochloride was dissolved in the polymer solution mixture. In vitro dissolution studies were preformed as illustrated in FIG. 2.

Example 3 (TP120)

Figure 3:
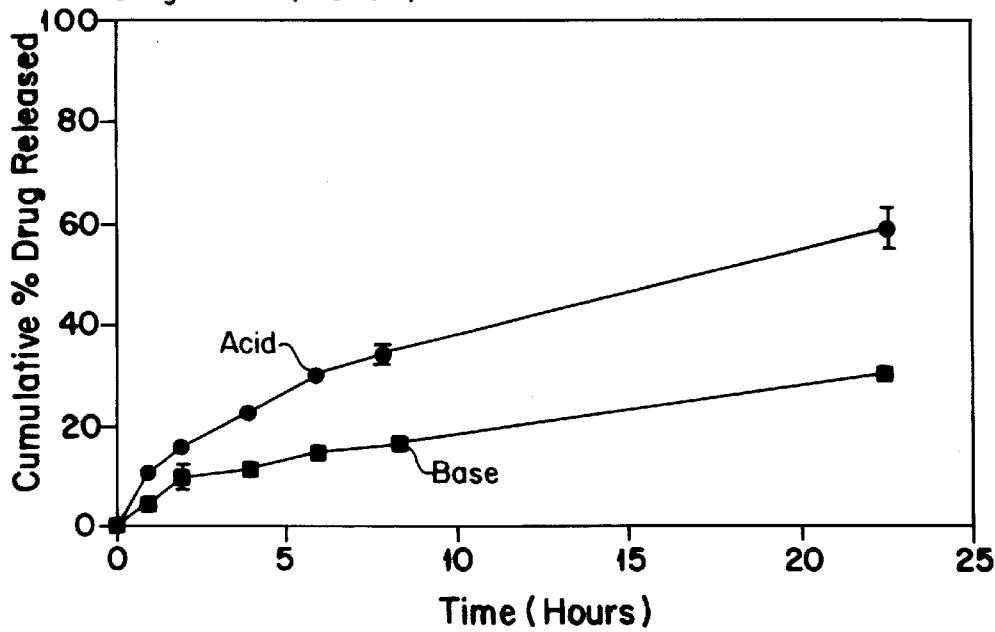

Method as in Example 1 with (a) 20 g of a 10% solution of vinyl pyrrolidone/vinyl acetate copolymer in water, (b) 10 g of a 2% solution of poly(acrylic acid) in water, (c) 100 g of a 2% solution of gum arabic in water. 6 g verapamil hydrochloride was dissolved in 150 ml ethanol (ethanol acts as the volatile complexation inhibitor). To this solution was added (a), then (b) and then (c). In vitro dissolution studies were preformed as illustrated in FIG. 3.

Example 4 (TP121 and TP142)

Figure 4:
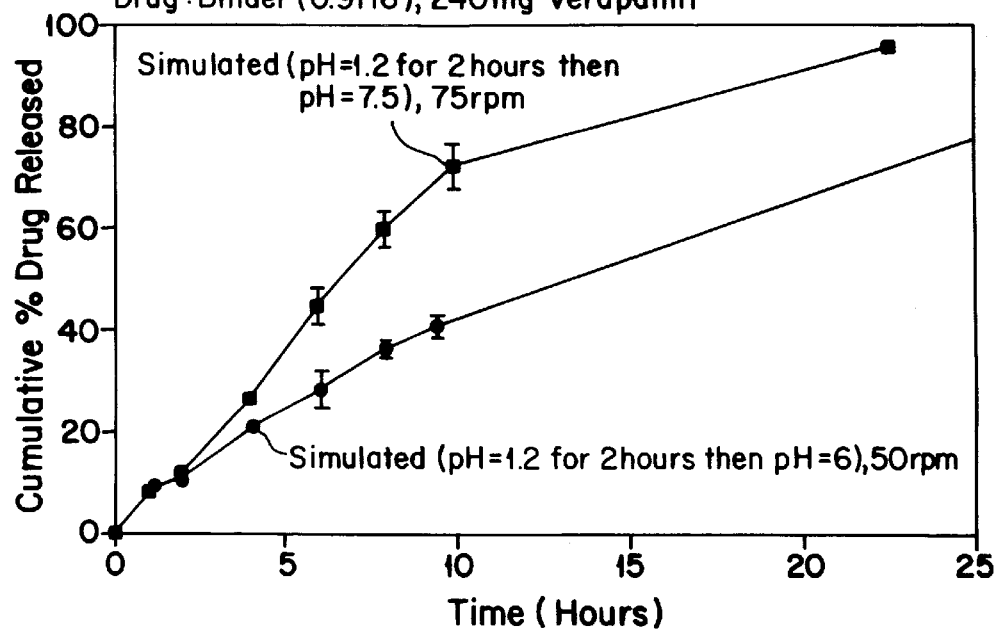
Figure 23:
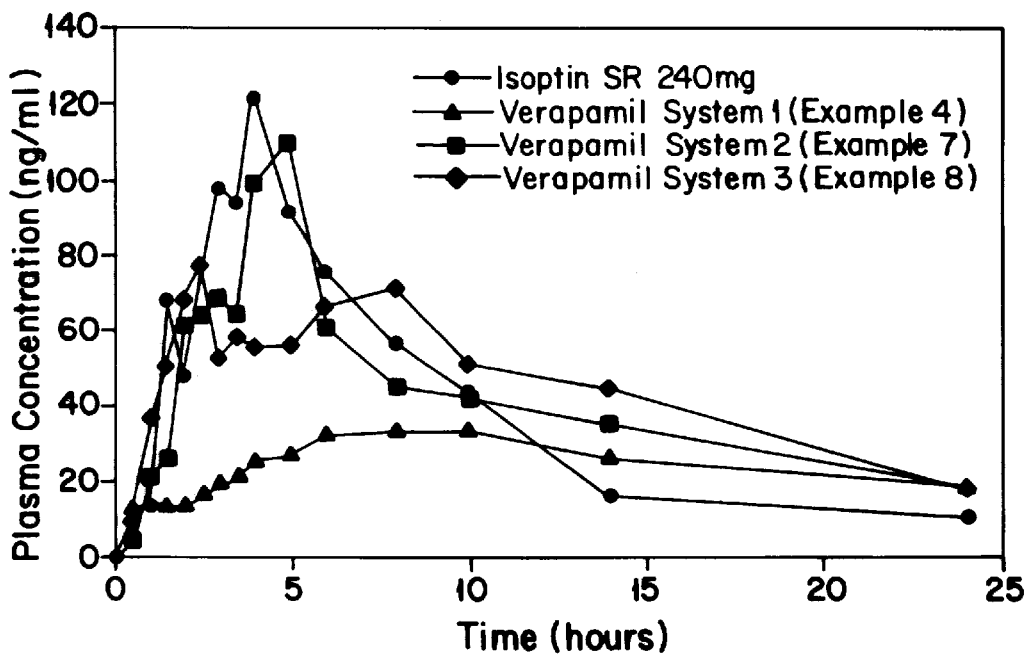
FIG. 23 shows the in vivo results of Examples 4, 7 and 8.

Method as in Example 1 with (a) 1 300 g of a 2% solution of vinyl methyl ether/maleic anhydride copolymer in water, (b) 1 300 g of a 2% solution of vinyl pyrrolidone/vinyl acetate copolymer in water and, (c) 1 300 g of a 2% solution of gum arabic in water. 78 g verapamil was added to the premixed polymer solution followed by the addition of 1 l acetone and 1 l ethanol, the latter two solvents act as the volatile complexation inhibitor. In vitro dissolution studies were preformed as illustrated in FIG. 4. In vivo results are shown in FIG. 23, after single dose administration to human volunteers (n=6).

Spray-drying Parameters

| Inlet Temperature | 139–140° C. |
|---|---|
| Outlet Temperature | 88–89° C. |
| Air flow | 600 Nl/h |
| Peristaltic Pump Speed | 540 ml/h |

Example 5 (TP123)

Method as in Example 1 with (a) 20 g of a 10% solution of vinyl pyrrolidone/vinyl acetate copolymer in water, (b)

Figure 5:
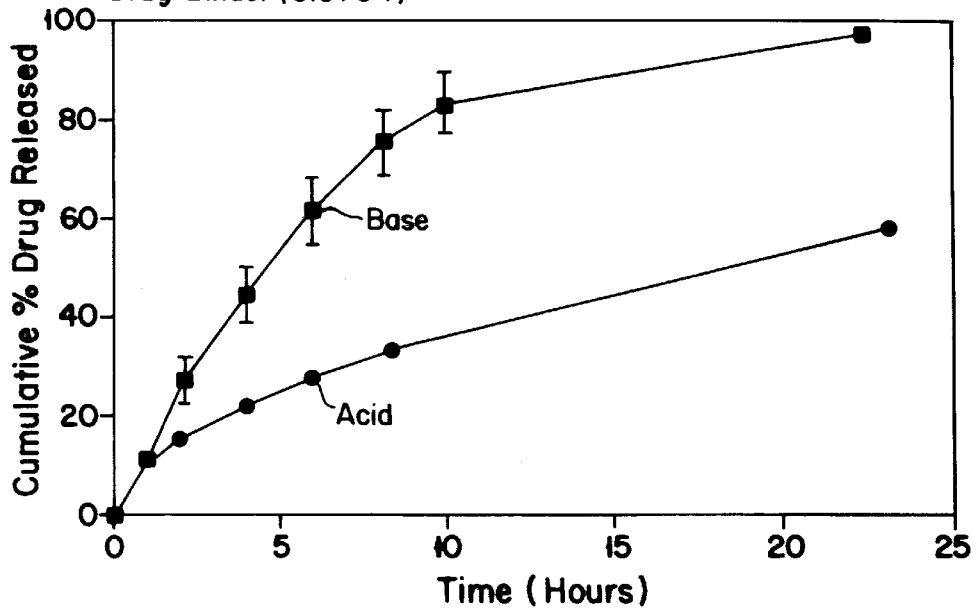

100 g of a 2% solution of poly(acrylic acid), and (c) 100 g of a 2% solution of gum arabic in water. 6 g verapamil was dissolved in 100 ml ethanol. To this was added (a) and (c). Then 100 ml acetone was added as a volatile complexation inhibitor. To this mixture was added (b). In vitro dissolution studies were performed as illustrated in FIG. 5.

Example 6 (TP240)

Figure 6:
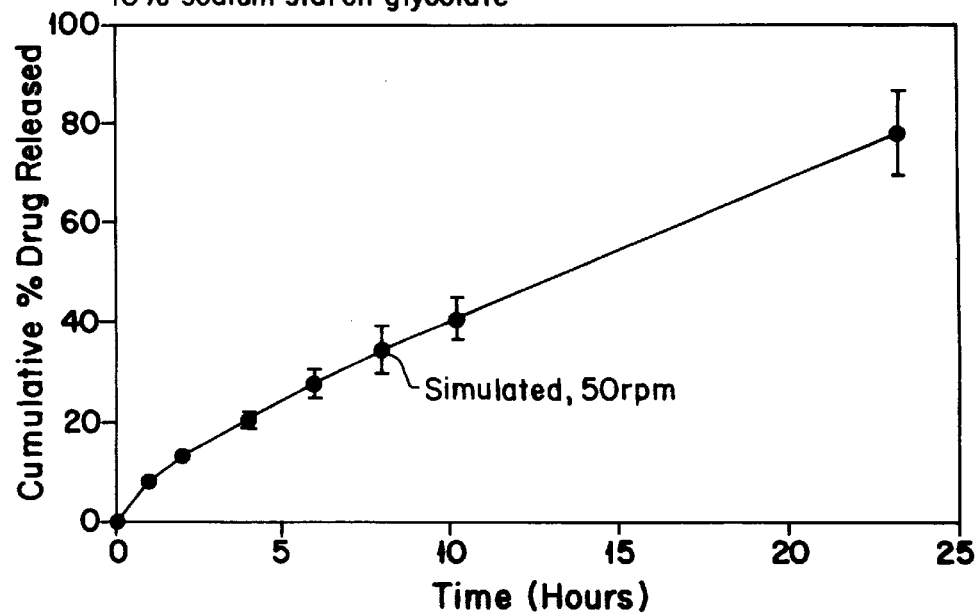

Method as in Example 1 with (a) 49 g of a 10% solution of vinyl methyl ether/maleic acid copolymer in water, (b) 21 g of a 10% solution of vinyl pyrrolidone/vinyl acetate copolymer in water. 7 g verapamil was dissolved in a mixture of 150 ml water and 100 ml acetone, the latter as a volatile complexation inhibitor. To this was added (a) and then (b). In vitro dissolution studies were preformed as illustrated in FIG. 6.

Example 7 (TP267)

Figure 7:
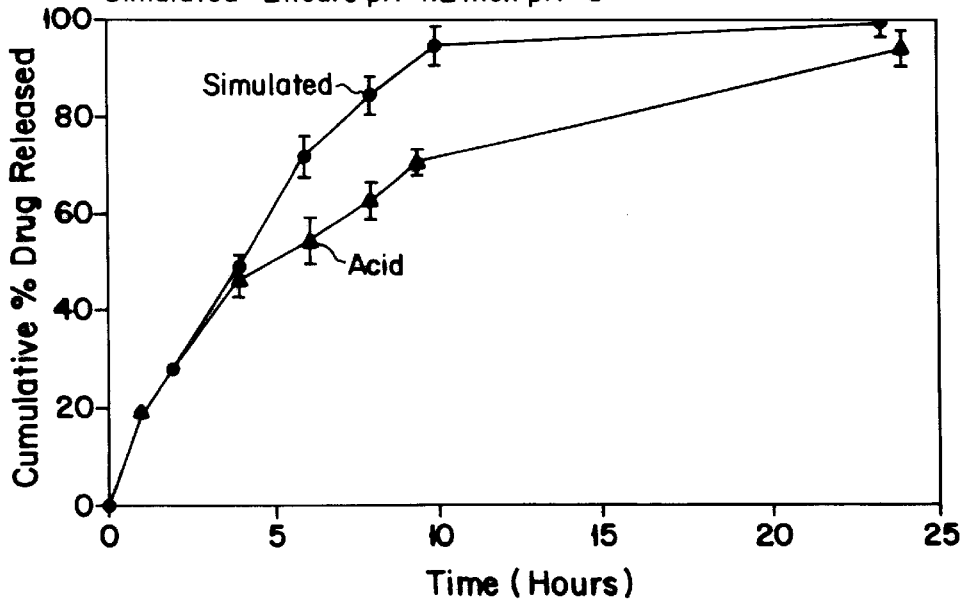
Figure 8:
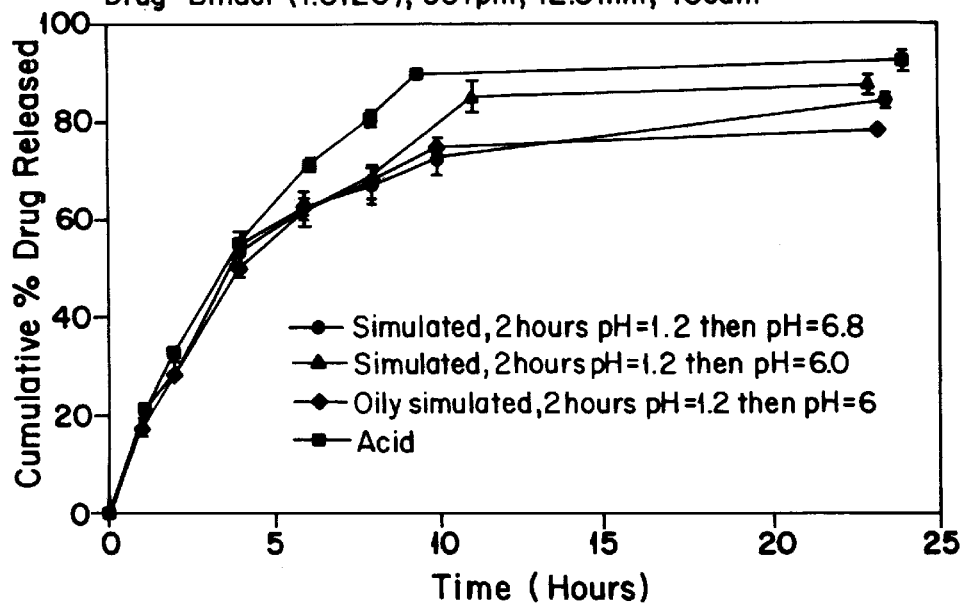

Method as in Example 1 with (a) 140 g of a 5% solution of sodium alginate in water, (b) 140 g of a 5% solution of vinyl pyrrolidone/vinyl acetate copolymer in water and, (c) 140 g of a 5% solution of hydroxypropyl methylcellulose in water. 21 g verapamil was dissolved in 400 ml water and added to the premixed polymer solution followed by the addition of 300 ml acetone. In vitro dissolution studies were preformed as illustrated in FIG. 7. In vivo results are shown in FIG. 23.

Spray-drying Parameters

| Inlet Temperature | 141° C. |
| Outlet Temperature | 94° C. |
| Air flow | 600 Nl/h |
| Peristaltic Pump speed | 180 ml/h |

Example 8 (TP283)

Figure 14:
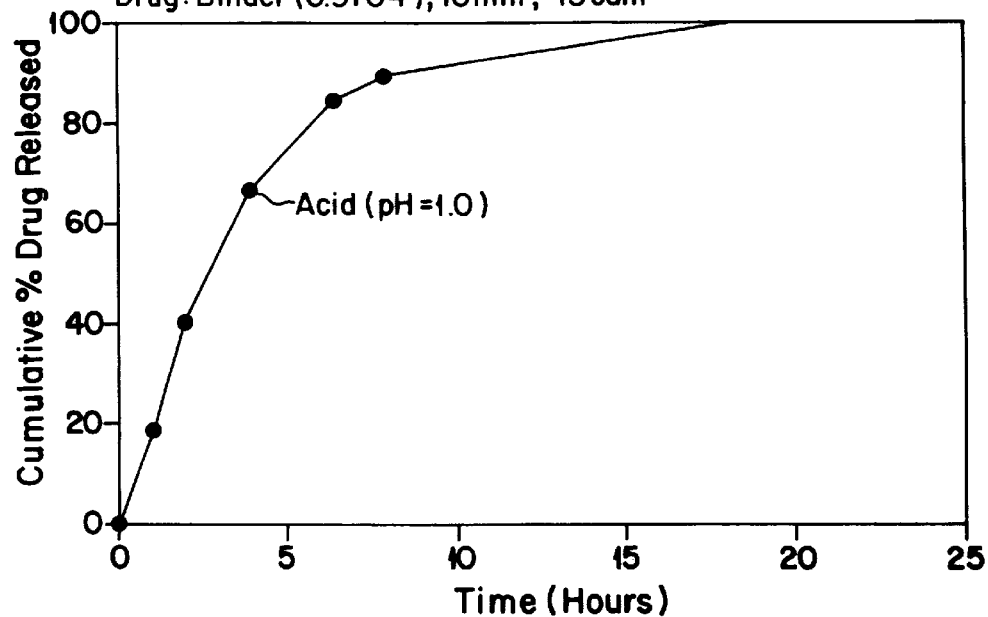

Method as in Example 1 with (a) 25 g of a 10% solution of poly(methacrylic acid-co-methylmethacrylate) in n-propanol and, (b) 225 g of a 10% solution of hydroxypropyl methycellulose in water. 37.5 g verapamil was dissolved in a mixture of solution (b) and 300 ml acetone followed by the addition of solution (a) to the mixture. In vitro dissolution studies were preformed as illustrated in FIG. 14. In vivo results are shown in FIG. 23.

Spray-drying Parameters

| Inlet Temperature | 140° C. |
| Outlet Temperature | 90–96° C. |
| Air flow | 500–600 Nl/h |
| Peristaltic Pump speed | 420 ml/h |

Example 9 (TP162)

Figure 9:
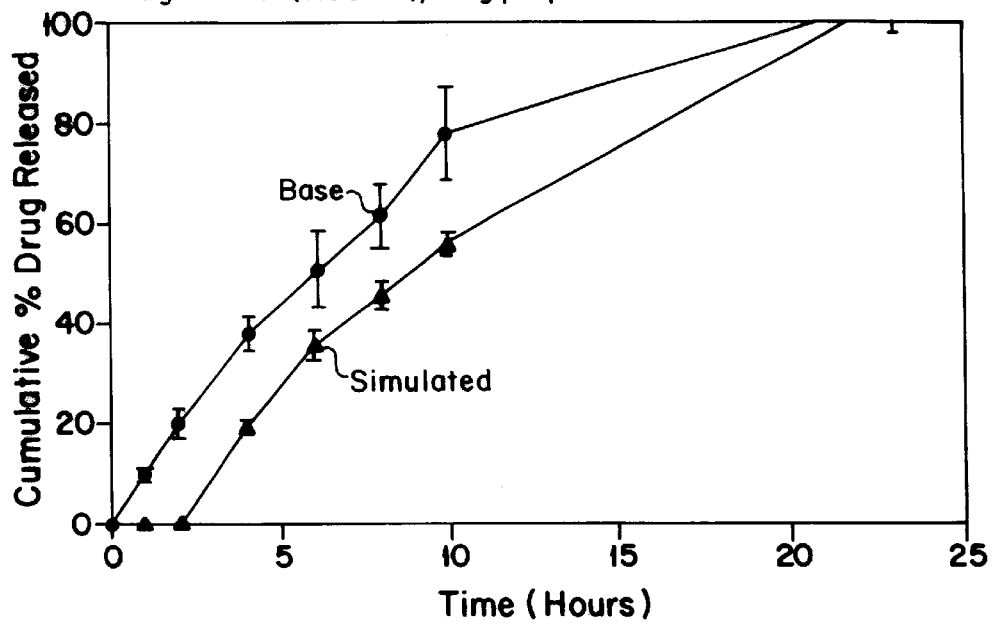

Method as in Example 1 with (a) 15 g of a 10% solution of poly(acrylic acid) in water, (b) 15 g of a 10% solution of vinyl pyrrolidone/vinyl acetate copolymer in water and (c) 15 g of a 10% solution of hydroxypropylcellulose in water. 4 g diclofenac was dissolved in a mixture of acetone and ethanol (150 ml of each) and 100 ml water was added to the system before spray drying. In vitro dissolution studies were performed as illustrated in FIG. 9.

Example 10 (TP316)

Figure 10:
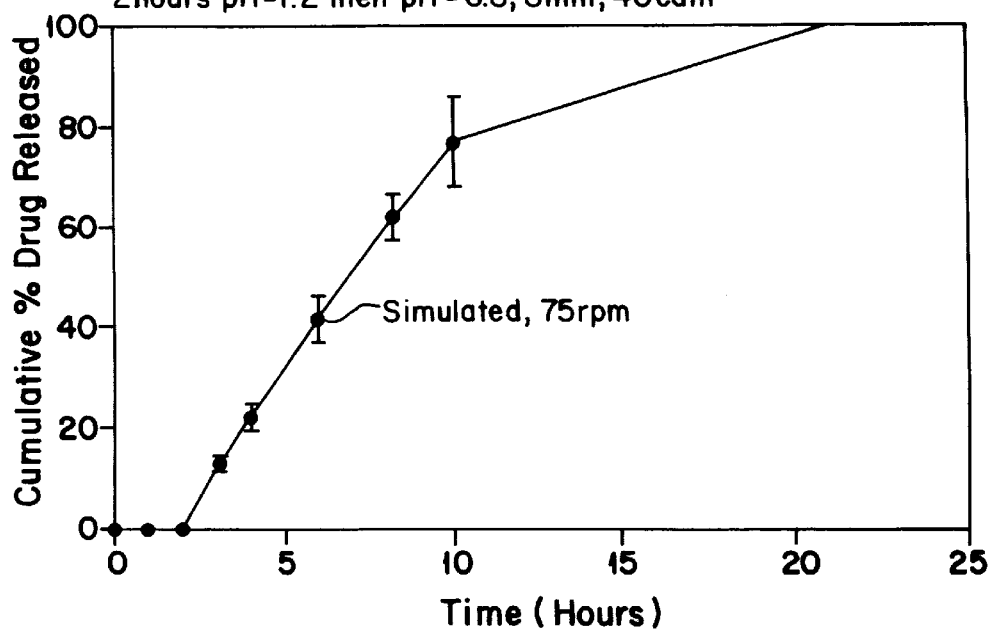

Method as in Example 1 with (a) 1.5 g of a 10% solution of methyl methacrylate/methacrylic acid copolymer in a 40:60 mixture of water:acetone, (b) 19.5 g of a 10% solution of vinyl pyrrolidone/vinyl acetate copolymer in water, and (c) 9 g of a 10% solution of hydroxypropylmethyl cellulose in water. 3 g Diclofenac was dissolved in 50 ml acetone, the acetone acts as a volatile complexation inhibitor. To this was added (a), then (b) and then (c). In vitro dissolution studies were performed as illustrated in FIG. 10.

Example 11 (TP282)

Figure 11:
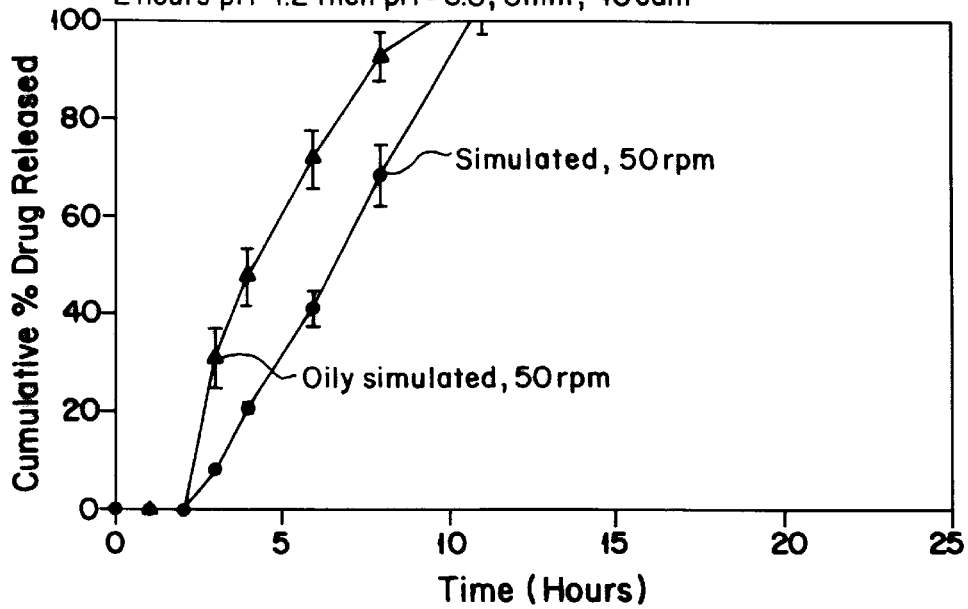
Figure 24:
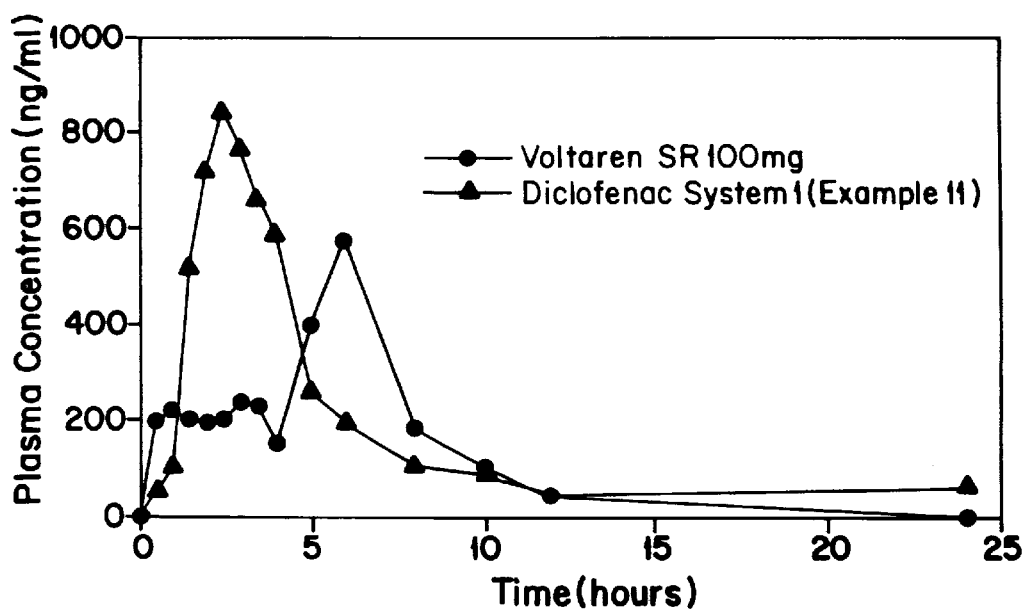
FIG. 24 is the in vivo result of the product of Example 11.

Method as in Example 1 with (a) 200 g of a 2.5% solution of sodium alginate in water, (b) 100 g of a 5% solution of vinyl pyrrolidone/vinyl acetate in water and, (c) 100 g of a 5% solution of hydroxypropyl methylcellulose in water. 15 g diclofenac was dissolved in 300 ml acetone and added to the premixed polymer solution. In vitro dissolution studies were performed as illustrated in FIG. 11. In vivo results are shown in FIG. 24, after single dose administration to human volunteers.

Spray-drying Parameters

| Inlet Temperature | 140° C. |
| Outlet Temperature | 90° C. |
| Air flow | 600 Nl/h |
| Peristaltic Pump speed | 240 ml/h |

Example 12 (TP21 and TP22)

Figure 12:
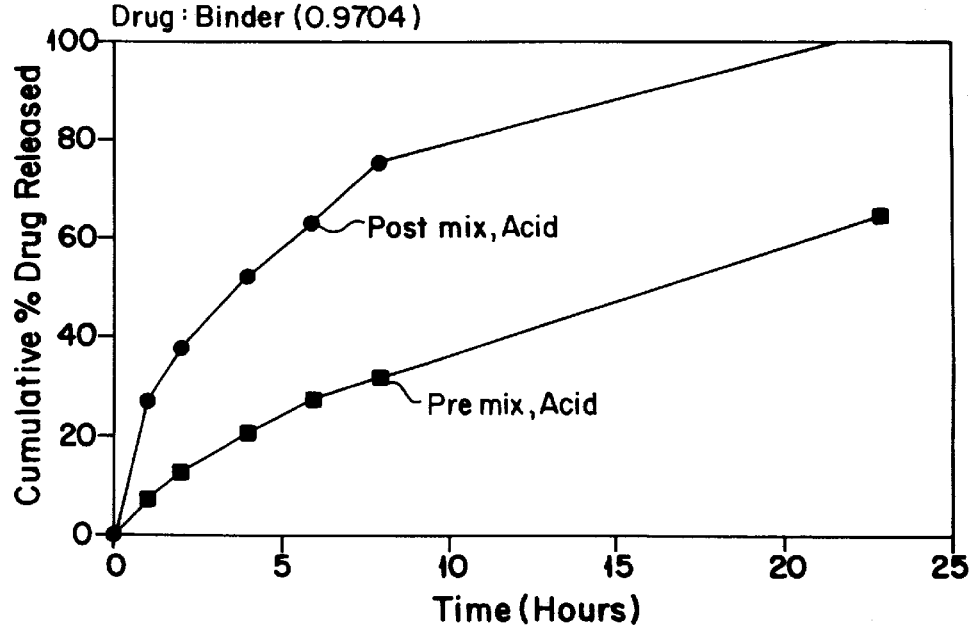

Method as in Example 1 with (a) 100 g of a 1% solution of poly(vinyl pyrrolidone) in water, (b) 100 g of a 1% solution of poly(ethylene oxide) in water and, (c) 100 g of a 1% solution of poly(acrylic acid) in water. Pre-mix: 3 g verapamil was dissolved in solution (c), admixed with solution (a) and (b), 150 ml acetone was added as a complexation inhibitor and the mixture was spray dried. Post-mix: solution (a), (b) and (c) were mixed, 150 ml acetone was added as a complexation inhibitor and the mixture was spray dried. Then 3 g verapamil was post mixed with the interpolymer complex powder. In vitro dissolution studies were performed as illustrated in FIG. 12. Notice the difference in the release profiles.

Example 13 (TP13)

Figure 13:
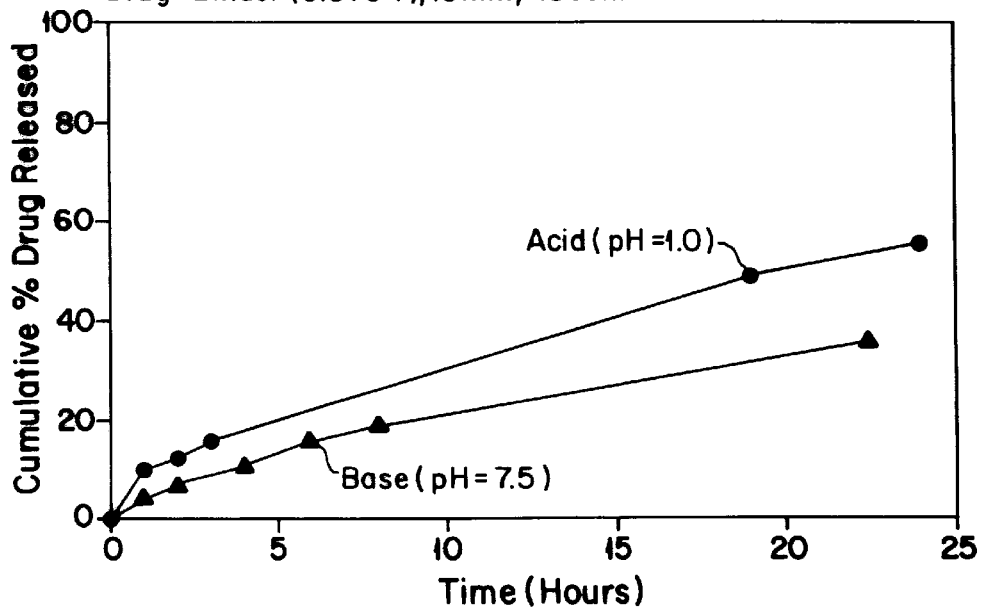

Method as in Example 1 with (a) 60 g of a 2% solution of methyl vinyl ether/maleic anhydride copolymer in water and, (b) 140 g of a 2% solution of vinyl pyrrolidone/vinyl acetate copolymer in ethanol. 4 g verapamil was dissolved in solution (b), admixed with solution (a) and the mixture was spray dried. In vitro dissolution studies were performed as illustrated in FIG. 13.

Example 14 (TP40)

Method as in Example 1 with (a) 100 g of a 2% solution of methyl vinyl ether/maleic anhydride copolymer in water and, (b) 100 g of a 2% solution of vinyl pyrrolidone/vinyl acetate copolymer in ethanol. 4 g verapamil is dissolved in solution (b), admixed with solution (a) and the mixture was spray dried. In vitro dissolution studies were performed as illustrated in FIG. 14.

Example 15 (TP43)

Figure 15:
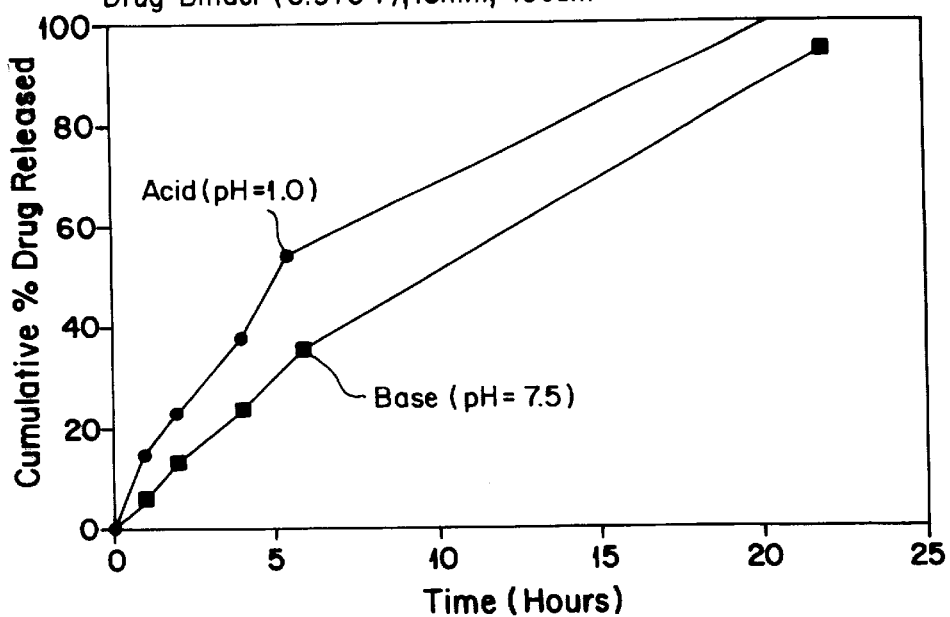

Method as in Example 1 with (a) 100 g of a 2% solution of poly(acrylic acid) in a water:ethanol (1:1) mixture and, (b) 100 g of a 2% solution of hydroxyethylcellulose in water. 4 g verapamil is dissolved in solution (a), admixed with solution (b) and the mixture was spray dried. In vitro dissolution studies were performed as illustrated in FIG. 15.

Example 16 (TP45)

Figure 16:
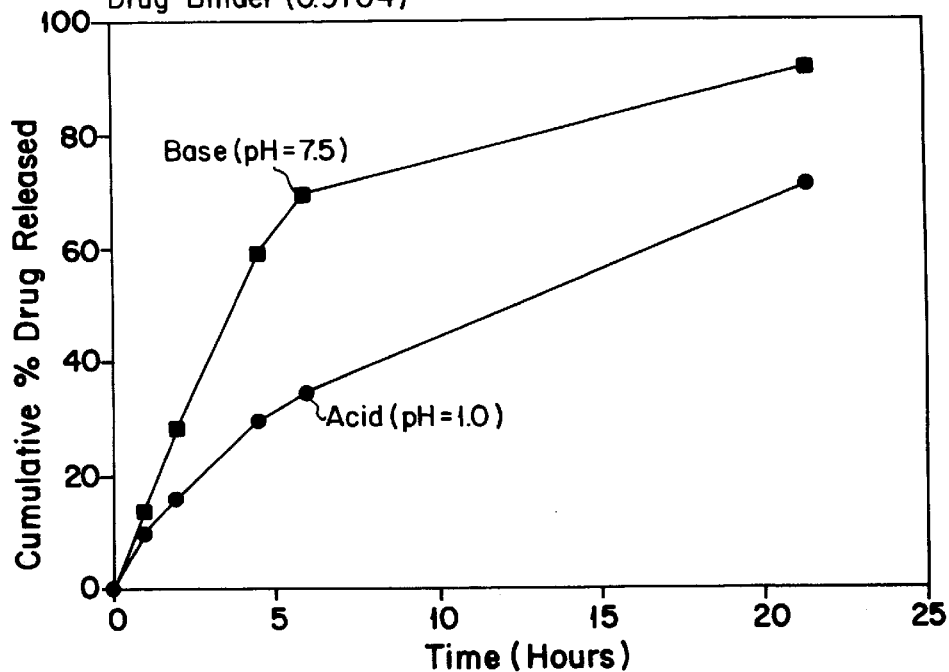

The following solutions were prepared: (a) 100 g of a 2% solution of methyl vinyl ether/maleic anhydride copolymer in water, (b) 100 g of a 2% solution of gum arabic in water, (c) 100 g of a 2% solution of vinyl pyrrolidone/vinyl acetate copolymer (60:40) in ethanol and, (d) a solution of 6 g verapamil in ethanol. The solutions (a) (b) and (c) were admixed, mixed with the solution (d) and spray dried. The spray dried granules were compressed into a tablet and in vitro dissolution studies were performed in acid (0.1M HCl) and base (phosphate buffer pH 7.5) as illustrated in FIG. 16.

Example 17 (TP49)

Figure 17:
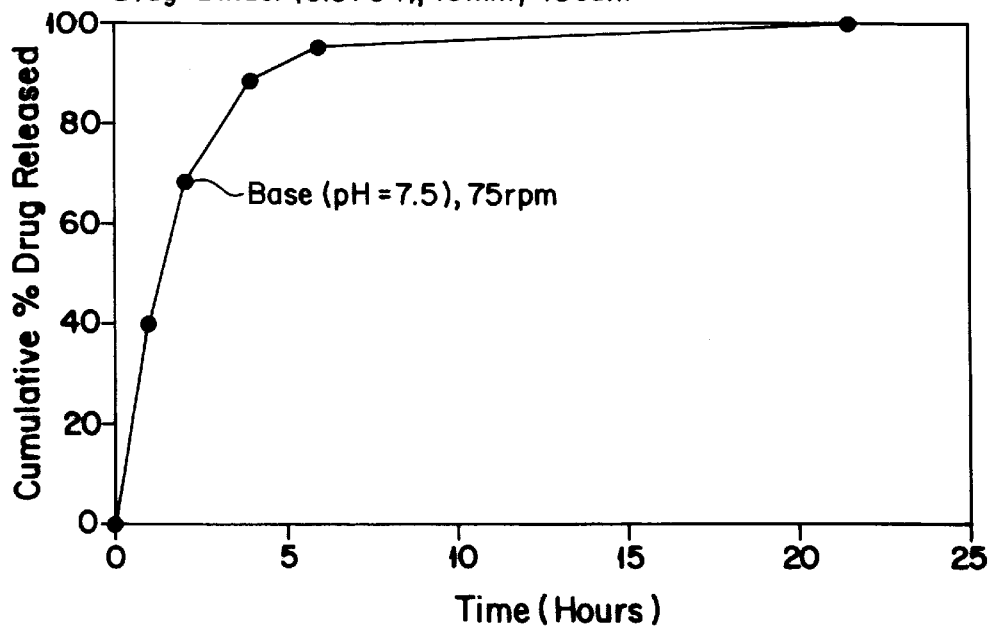

Method as in Example 1 with (a) 100 g of a 2% solution of methyl vinyl ether/maleic anhydride copolymer in water and, (b) 100 g of a 2% solution of hydroxypropylcellulose in water. 4 g indomethacin was slurried in 50 ml ethanol, mixed with solutions (a) and (b) and the mixture was spray dried. In vitro dissolution studies were performed as illustrated in FIG. 17.

Example 18 (TP60)

Figure 18:
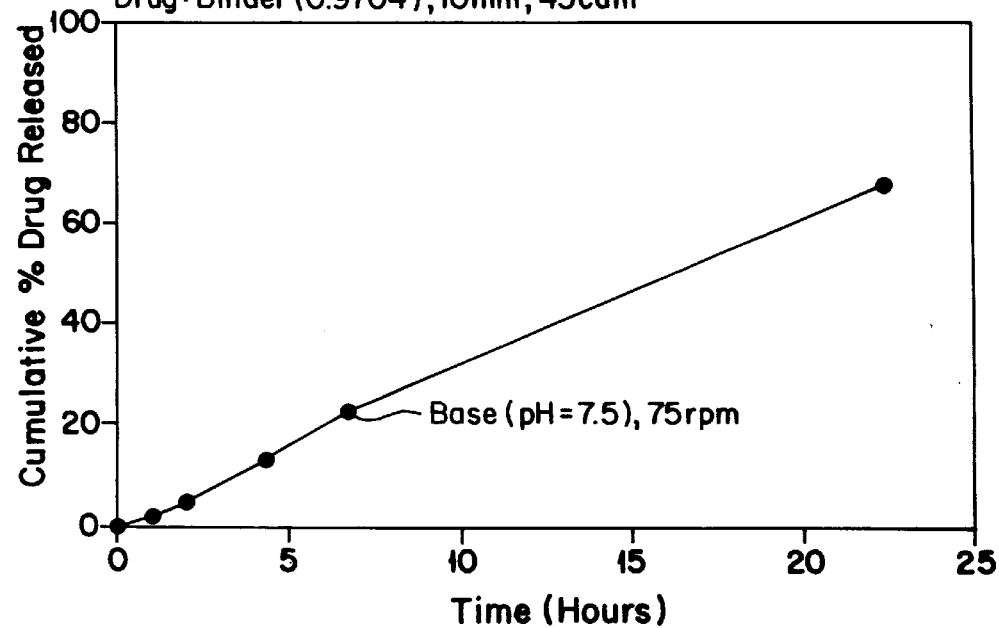

Method as in Example 14 with sodium diclofenac in place of verapamil. In vitro dissolution studies were performed as illustrated in FIG. 18.

Example 19 (TP66)

Figure 19:
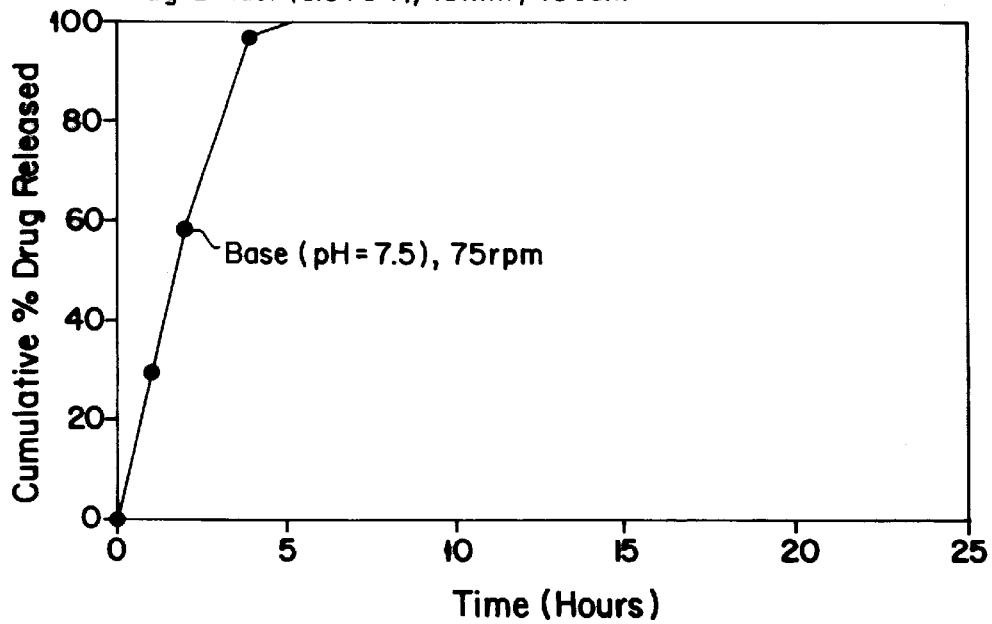

Method as in Example 1 with (a) 97% of a 2% solution of methyl vinyl ether/maleic anhydride copolymer in water and, (b) 97 g of a 2% solution of sodium carboxymethylcellulose in water. 3.88 g sodium diclofenac was dissolved in 50 ml ethanol and admixed with solutions (a) and (b) and the mixture was spray dried. In vitro dissolution studies were performed as illustrated in FIG. 19.

Example 20 (TP73)

Figure 20:
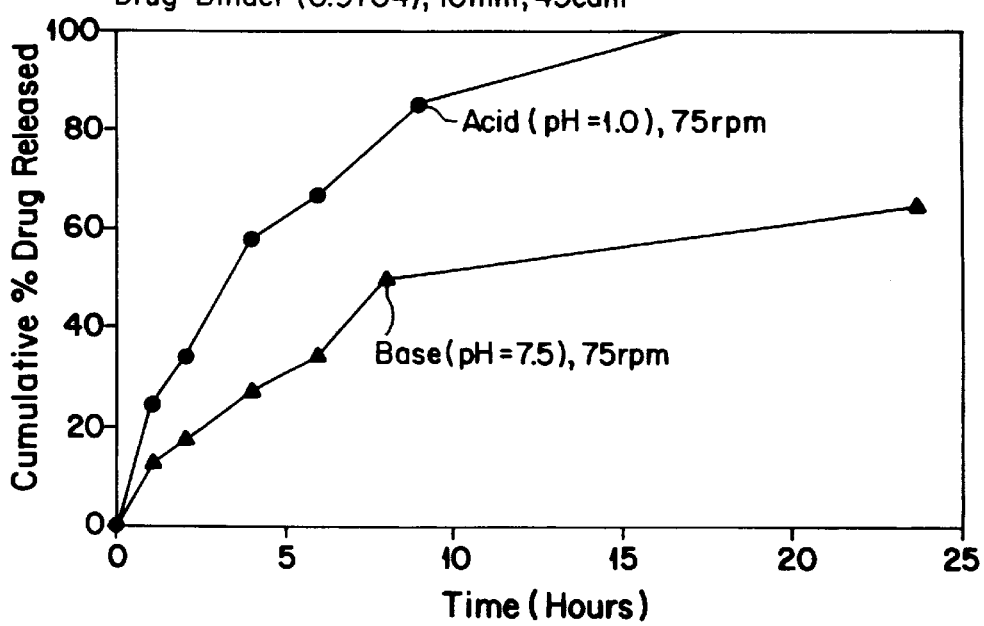

Method as in Example 1 with (a) 100 g of a 2% solution of poly(vinyl alcohol) in water and, (b) 100 g of a 2% solution of poly(ethylene oxide) in water: ethanol (1:1). 4 g diltiazem was dissolved in the mixture of solutions (a) and (b) and the mixture was spray dried. In vitro dissolution studies were performed as illustrated in FIG. 20.

Example 21 (TP76)

Figure 21:
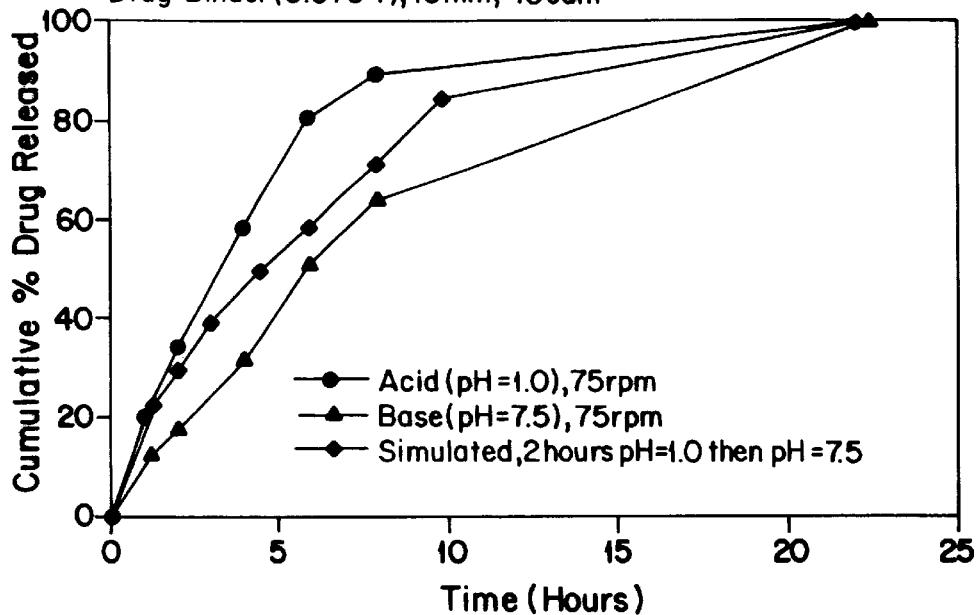

Method as in Example 1 with (a) 64 g of a 2% solution of poly(acrylic acid) in water:ethanol (1:1), (b) 64 g of a 2% solution of poly(ethylene oxide) in water and, (c) 64 g of a 2% solution of hydroxyethylcellulose in water. 3.84 g diltiazem was dissolved in a mixture of solutions (b) and (c), admixed with solution (a) and the mixture was spray dried. In this example ethanol acts as the complexation inhibitor. In vitro dissolution studies were performed as illustrated in FIG. 21.

Example 22 (TP343)

Figure 22:
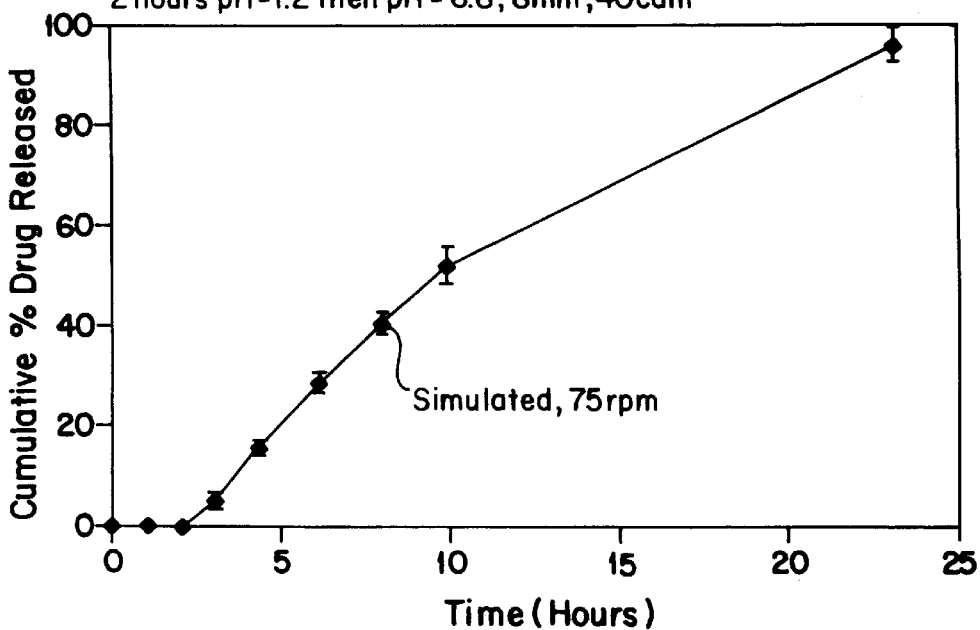

Method as in Example 1 with (a) 10 g of a 10% dispersion of methyl methacrylate/methacrylic acid copolymer, (b) 10 g of a 10% solution of vinyl pyrrolidone/vinyl acetate copolymer in water and, (c) 10 g of a 10% solution of hydroxypropylmethylcellulose in water. 3.09 g diclofenac was preprotonated, filtered and washed with distilled water before redissolving it in 50 ml acetone. The drug solution was added to (a) which became a clear solution, then admixed with (b) and (c) and spray dried. In this example acetone acts as the complexation inhibitor. In vitro dissolution studies are performed as illustrated in FIG. 22.

TABLE 2

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
|---|---|---|---|
| TP6 | Verapamil (1:5.25) | PVME/MA S-97:PVP/VAc E-635 (1:1)<br>(a) 100 g of 5% vinyl methyl ether/maleic acid copolymer in water<br>(b) 100 g of 5% vinyl pyrrolidone/vinyl acetate copolymer (60:40) in ethanol | |
| TP7 | Verapamil (1:1) | PVME/MA S-97:PVP/VAc E-635 (1:1)<br>(a) 100 g of 2% vinyl methyl ether/maleic acid copolymer in water<br>(b) 100 g of 2% vinyl pyrrolidone/vinyl acetate copolymer in (60:40) in ethanol | |
| TP8 | Verapamil (1:1) | PVME/MA S-97:PVP/VAc E-535 (30:70)<br>(a) 60 g of 2% vinyl methyl ether/maleic acid copolymer in water<br>(b) 140 g of 2% vinyl pyrrolidone/vinyl acetate copolymer in (50:50) in ethanol | |
| TP10 | Verapamil (1:1) | PVME/MA S-97:PVP/VAc E-535 (5:95)<br>(a) 10 g of 2% vinyl methyl ether/maleic acid copolymer in water<br>(b) 190 g of 2% vinyl pyrrolidone/vinyl acetate copolymer in (50:50) in ethanol | |
| TP11 | Verapamil (1:5.25) | PVME/MA S-97:PVP/VAc E-635 (1:1)<br>(a) 100 g of 5% vinyl methyl ether/maleic acid copolymer in water<br>(b) 100 g of 5% vinyl pyrrolidone/vinyl acetate copolymer in (60:40) in ethanol<br>(c) 10% microcrystalline cellulose postmixed | 10% microcrystalline cellulose post mixed |
| TP12 | Verapamil (1:1) | PVME/MA S-97:PVP/VAc E-535 (30:70)<br>(a) 60 g of 2% vinyl methyl ether/maleic acid copolymer in water<br>(b) 140 g of 2% vinyl pyrrolidone/vinyl acetate copolymer in (50:50) in ethanol<br>(c) 10% starch postmixed | 10% starch post mixed |

TABLE 2-continued

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
|---|---|---|---|
| TP13 | Verapamil (1:1) | PVME/MA S-97:PVP/VAc E-335 (30:70) | |
| TP14 | Verapamil (1:1) | PVME/MA S-97:PVP/VAc E-335 (30:70)<br>(a) 60 g of 2% vinyl methyl ether/maleic acid copolymer in water<br>(b) 140 g of 2% vinyl pyrrolidone/vinyl acetate copolymer in (30:70) in ethanol<br>(c) 10% of crospovidone postmixed | 10% crospovidone post mixed |
| TP15 | Verapamil (1:1) | PVP K90:PAA K752 (90:10)<br>(a) 180 g of 2% poly(vinyl pyrrolidone) in water<br>(b) 20 g of 2% poly(acrylic acid) in water | |
| TP16 | Verapamil (1:1) | PVME/MA S-97:PVP/VAc E-535 (20:80)<br>(a) 40 g of 2% vinyl methyl ether/maleic acid copolymer in water<br>(b) 160 g of 2% vinyl pyrrolidone/vinyl acetate copolymer in (30:70) in ethanol | |
| TP17 | Verapamil (1:1) | PVME/MA S-97:PVP/VAc E-335 (40:60)<br>(a) 80 g of 2% vinyl methyl ether/maleic acid copolymer in water<br>(b) 120 g of 2% vinyl pyrrolidone/vinyl acetate copolymer in (30:70) in ethanol | |
| TP18 | Verapamil (1:1) | PVME/MA S-97:PVP/VAc E-535 (1)<br>(a) 100 g of 2% vinyl methyl ether/maleic acid copolymer in water<br>(b) 100 g of 2% vinyl pyrrolidone/vinyl acetate copolymer in (30:70) in ethanol | |
| TP19 | Verapamil (1:1) | PVME/MA S-97:PVP/VAc E-335 (20:80)<br>(a) 40 g of 2% vinyl methyl ether/maleic acid copolymer in water<br>(b) 160 g of 2% vinyl pyrrolidone/vinyl acetate copolymer in (30:70) in ethanol | |
| TP20 | Verapamil (1:1) | PVP K90:PAA K752 (20:80)<br>(a) 160 g of 2% poly(vinyl pyrrolidone) in water<br>(b) 40 g of 2% poly(acrylic acid) in water | |
| TP21 | Verapamil (1:1) | PVP K90:PEO N10:PAA K752 (1:1:1) | Post mixed |
| TP22 | Verapamil (1:1) | PVP K90:PEO N10:PAA K752 (1:1:1) | Same as TP21 |
| TP23 | Verapamil (1:1) | PVME/MA S-97:PVP/VAc E-535 (40:60)<br>(a) 80 g of 2% vinyl methyl ether/maleic acid copolymer in water<br>(b) 120 g of 2% vinyl pyrrolidone/vinyl acetate copolymer in (50:50) in ethanol | |
| TP24 | Verapamil (1:1) | PVME/MA S-97:PVP/VAc E-635 (20:80)<br>(a) 40 g of 2% vinyl methyl ether/maleic acid copolymer in water<br>(b) 160 g of 2% vinyl pyrrolidone/vinyl acetate copolymer in (60:40) in ethanol | |
| TP25 | Verapamil (1:1) | PVME/MA S-97:PVP/VAc E-635 (30:70)<br>(a) 60 g of 2% vinyl methyl ether/maleic acid copolymer in water<br>(b) 140 g of 2% vinyl pyrrolidone/vinyl acetate copolymer in (60:40) in ethanol | |
| TP27 | Verapamil (1:1) | PVP K90:PAA K752 (50:50)<br>(a) 100 g of 2% poly(vinyl pyrrolidone) in water<br>(b) 100 g of 2% poly(acrylic acid) in water | |
| TP28 | Verapamil (1:1) | PVME/MA S-97:PVP/VAc E-535 (15:85)<br>(a) 170 g of 2% vinyl pyrrolidone/vinyl acetate copolymer (50:50) in water<br>(b) 30 g of 2% vinyl methyl ether/maleic acid copolymer in water | |
| TP29 | Verapamil (1:1) | PVME/MA S-97:PVP/VAc E-535 (15:85)<br>(a) 170 g of 2% vinyl pyrrolidone/vinyl acetate copolymer (50:50) in ethanol<br>(b) 30 g of 2% vinyl methyl ether/maleic acid copolymer in water<br>(c) drug post mixed | Post mixed |
| TP30 | Verapamil (1:1) | PVME/MA S-97:PVP/VAc E-635 (40:60)<br>(a) 80 g of 2% vinyl methyl ether/maleic acid copolymer in water<br>(b) 120 g of 2% vinyl pyrrolidone/vinyl acetate copolymer in (60:40) in ethanol | |
| TP32 | Verapamil (1:1) | PVME/MA S-97:PVP/VAc E-535 (50:50)<br>(a) 100 g of 2% vinyl methyl ether/maleic acid copolymer in water<br>(b) 100 g of 2% vinyl pyrrolidone/vinyl acetate copolymer in (30:70) in ethanol | |
| TP33 | Verapamil (1:1) | PVME/MA S-97:PVP/VAc E-535 (20:80)<br>(a) 160 g of 2% vinyl pyrrolidone/vinyl acetate copolymer in (50:50) in ethanol<br>(b) 40 g of 2% vinyl methyl ether/maleic acid copolymer in water | |
| TP35 | Verapamil (1:1) | PVME/MA S-97:PVA 165 (1:1)<br>(a) 100 g of 2% poly(vinyl alcohol) in water<br>(b) 100 g of 2% vinyl methyl ether/maleic acid copolymer in water<br>(c) drug post mixed | Post mixed |

TABLE 2-continued

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
| --- | --- | --- | --- |
| TP36 | Verapamil (1:1) | PVME/MA S-97:PVP/VAc E-635 (30:70)<br>(a) 60 g of 2% vinyl methyl ether/maleic acid copolymer in water<br>(b) 140 g of 2% vinyl pyrrolidone/vinyl acetate copolymer (60:40) in ethanol | 10% crospovidone post mixed |
| TP37 | Verapamil (1:1) | PVME/MA S-97:PVP/VAc E-335 (10:90)<br>(a) 60 g of 2% vinyl methyl ether/maleic acid copolymer in water<br>(b) 140 g of 2% vinyl pyrrolidone/vinyl acetate copolymer (60:40) in ethanol | |
| TP38 | Verapamil (1:1) | PVP K90:PEO N750:PAA K752 (42:18:40)<br>(a) 80 g of 2% poly(acrylic acid) in water/ethanol (1:1)<br>(b) 36 g of 2% poly(ethylene oxide) in water<br>(c) 84 g of 2% poly(vinyl pyrrolidone) in water | |
| TP39 | Verapamil (1:1) | PVME/MA S-97:Gum Arabic (1:1)<br>(a) 100 g of 2% gum arabic in water<br>(b) 100 g of 2% vinyl methyl ether/maleic acid copolymer in water | |
| TP40 | Verapamil (1:1) | PVME/MA S-97:PVP/VAc E-735 (1:1) | |
| TP41 | Verapamil (1:1) | PVAc UW1<br>(a) 200 g of 2% polyvinyl acetate in ethanol | |
| TP42 | Verapamil (1:1) | PVME/MA S-97:PVP/VAc E-535 (20:80)<br>(a) 160 g of 2% vinyl pyrrolidone/vinyl acetate copolymer (50:50) in ethanol<br>(b) 40 g of 2% vinyl methyl ether/maleic acid copolymer in water | Repeat of TP33 |
| TP43 | Verapamil (1:1) | PAA K752:HEC 250HX (1:1) | |
| TP44 | Verapamil (1:1) | PVME/MA S-97:HEC 250HX (1:1)<br>(a) 100 g of 2% vinyl methyl ether/maleic acid copolymer in water<br>(b) 100 g of 2% hydroxyethyl cellulose in water | |
| TP45 | Verapamil (1:1) | PVME/MA S-97:PVP/VAc E-635:Gum Arabic (1:1:1) | |
| TP46 | Verapamil (1:1) | PVP/VAc E-635:PEO N750:PAA K752 (1:1:1)<br>(a) 70 g of 2% poly(acrylic acid) in water<br>(b) 70 g of 2% poly(ethylene oxide) in water<br>(c) 70 g of 2% vinyl pyrrolidone/vinyl acetate copolymer (60:40) in ethanol | |
| TP47 | Verapamil (1:1) | PVME/MA S-97: HPC 99LF (1:1)<br>(a) 100 g of 2% vinyl methyl ether/maleic acid copolymer in water<br>(b) 100 g of 2% hydroxypropyl cellulose in water | |
| TP48 | Indomethacin (1:1) | PVME/MA S-97:PVP/VAc E-535 (20:80)<br>(a) 160 g of 2% vinyl pyrrolidone/vinyl acetate copolymer (50:50) in ethanol<br>(b) 40 g of 2% vinyl methyl ether/maleic acid copolymer in water | |
| TP49 | Indomethacin (1:1) | PVME/MA S-97:HPC 99LF (1:1) | |
| TP50 | Indomethacin (1:1) | PVA 107:PEO N10 (1:1) | |
| TP51 | Indomethacin (1:1) | PVP K90:PEO N10:PAA K752 (1:1:1)<br>(a) 70 g of 2% poly(ethylene oxide) in water<br>(b) 70 g of 2% poly(vinyl pyrrolidone) in water<br>(c) 70 g of 2% poly(acrylic acid) in water | |
| TP52 | Indomethacin (1:1) | PVME/MA S-97:PVP/VAc E-635 (1:1)<br>(a) 100 g of 2% vinyl pyrrolidone/vinyl acetate copolymer (60:40) in ethanol/water (1:1)<br>(b) 100 g of 2% vinyl methyl ether/maleic acid copolymer in water | |
| TP53 | Indomethacin (1:1) | PVME/MA S-97: NaCMC C30 (1:1)<br>(a) 100 g of 2% vinyl methyl ether/maleic acid copolymer in water<br>(b) 100 g of 2% sodium carboxymethyl cellulose in water | |
| TP54 | Indomethacin (1:1) | PAA K752:HEC 250HX (1:1)<br>(a) 100 g of 2% hydroxyethyl cellulose in water<br>(b) 100 g of 2% poly(acrylic acid) in water/ethanol (1:1) | |
| TP55 | Indomethacin (1:1) | PVP K90:PEO N750:PAA K752 (35:15:50)<br>(a) 70 g of 2% poly(vinyl pyrrolidone) in water<br>(b) 30 g of 2% poly(ethylene oxide) in water<br>(c) 100 g of 2% poly(acrylic acid) in water | |
| TP56 | Indomethacin (1:1) | PVME/MA S-97:PVP/VAc E-635 (40:60)<br>(a) 120 g of 2% vinyl pyrrolidone/vinyl acetate copolymer (60:40) in water/ethanol (1:1)<br>(b) 80 g of 2% vinyl methyl ether/maleic acid copolymer in water | |
| TP57 | Indomethacin (1:1) | PVME/MA S-97:PVP/VAc E-635 (30:70)<br>(a) 140 g of 2% vinyl pyrrolidone/vinyl acetate copolymer (60:40) in water/ethanol (1:1)<br>(b) 60 g of 2% vinyl methyl ether/maleic acid copolymer in water | |
| TP58 | Indomethacin (1:1) | PAA K752:PEO N10:PVP K90 (1:1:1) | |
| TP59 | Sodium Diclofenac (1:1) | PVA 107:PEO N10 (1:1)<br>(a) 100 g of 2% poly(vinyl alcohol) in water<br>(b) 100 g of 2% poly(ethylene oxide) in water | |

TABLE 2-continued

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
|---|---|---|---|
| TP60 | Sodium Diclofenac (1:1) | PAA K752:HEC 250HX (1:1) | |
| TP62 | Sodium Diclofenac (1:1) | PVME/MA S-97:PVP/VAc E-635 (1:1)<br>(a) 100 g of 2% vinyl pyrrolidone/vinyl acetate copolymer in water/ethanol (1:1)<br>(b) 100 g of 2% vinyl methyl ether/maleic acid copolymer in water | |
| TP63 | Sodium Diclofenac (1:1) | PVME/MA S-97:PVP/VAc E-635 (40:60)<br>(a) 120 g of 2% vinyl pyrrolidone/vinyl acetate copolymer (60:40) in water<br>(b) 80 g of 2% vinyl methyl ether maleic anhydride copolymer in water | |
| TP64 | Sodium Diclofenac (1:1) | PVP K90:PEO N750:PAA K752 (35:15:50)<br>(a) 100 g of 2% poly(acrylic acid) in water<br>(b) 70 g of 2% poly(vinyl pyrrolidone) in water<br>(c) 30 g of 2% poly(ethylene oxide) in water | |
| TP65 | Sodium Diclofenac (1:1) | PVP/VAc E-635:PEO N10:PVME/MA S-97 (1:1:1)<br>(a) 103.7 g of 2% vinyl pyrrolidone/vinyl acetate copolymer (60:40) in water/ethanol (1:1)<br>(b) 103.7 g of 2% vinyl methyl ether/maleic acid copolymer in water<br>(c) 103.7 g of 2% poly(ethylene oxide) in water | |
| TP66 | Sodium Diclofenac (1:1) | PVME/MA S-97:NaCMC C30 (1:1) | |
| TP67 | Sodium Diclofenac (1:1) | PVP K90:PEO N10:PAA K752 (1:1:1)<br>(a) 80 g of 2% poly(acrylic acid) in water<br>(b) 80 g of 2% poly(ethylene oxide) in water<br>(c) 80 g of 2% poly(vinyl pyrrolidone) in water | |
| TP68 | Sodium Diclofenac (1:1) | PVME/MA S-97:HPC 99LF (1:1)<br>(a) 100 g of 2% vinyl methyl ether/maleic acid copolymer in water<br>(b) 100 g of 2% hydroxypropyl cellulose in water | |
| TP69 | Sodium Diclofenac (1:1) | PAA K752:HEC 250HX:PEO N10 (1:1:1)<br>(a) 71 g of 2% poly(ethylene oxide) in water<br>(b) 71 g of 2% hydroxyethyl cellulose in water<br>(c) 71 g of 2% poly(acrylic acid) in water | |
| TP70 | Diltiazem (1:1) | PAA K752:HEC 250HX (1:1)<br>(a) 100 g of 2% poly(acrylic acid) in water<br>(b) 100 of 2% hydroxyethyl cellulose in water | |
| TP73 | Diltiazem (1:1) | PVA 107:PEO N10 (1:1) | |
| TP74 | Diltiazem (1:1) | PVME/MA S-97:PVP/VAc E-635 (1:1)<br>(a) 100 g of 2% vinyl methyl ether/maleic acid copolymer in water<br>(b) 100 g of 2% vinyl pyrrolidone/vinyl acetate copolymer (60:40) in ethanol | |
| TP75 | Diltiazem (1:1) | PVME/MA S-97:HPC 99LF (1:1)<br>(a) 100 g of 2% hydroxypropyl cellulose in water<br>(b) 100 g of 2% vinyl methyl ether/maleic acid copolymer in water | |
| TP76 | Diltiazem (1:1) | PAA K752:PEO N10:HEC 250HX (1:1:1) | |
| TP77 | Diltiazem (1:1) | PVME/MA S-97:PVP/VAc E-635:Gum Arabic (1:1:1)<br>(a) 70 g of 2% vinyl methyl ether/maleic acid copolymer in water<br>(b) 70 g of 2% vinyl pyrrolidone/vinyl acetate copolymer (60:40) in water<br>(c) 70 g of 2% gum arabic in water | |
| TP78 | Diltiazem (1:1) | PAA K752:PVP/VAc E-635:HEC 250HX (1:1:1)<br>(a) 70 g of 2% poly(acrylic acid) in water<br>(b) 70 g of 2% hydroxyethyl cellulose in water<br>(c) 70 g of vinyl pyrrolidone/vinyl acetate copolymer (60:40) in water/ethanol (1:1) | |
| TP79 | Diltiazem (1:1) | PAA K752:PVP K90:PEO N10 (1:1:1)<br>(a) 70 g of 2% poly(acrylic acid) in water<br>(b) 70 g of 2% poly(vinyl pyrrolidone) in water<br>(c) 70 g of 2% poly(ethylene oxide) in water | |
| TP80 | Verapamil (1:1) | PVME/MA S-97:PVP/VAc E-635 (1:1) | |
| TP81 | Verapamil (1:1) | PVA 107:PEO N10 (1:1)<br>(a) 99.2 g of 2% poly(ethylene oxide) in water<br>(b) 99.2 g of 2% poly(vinyl alcohol) in water | |
| TP82 | Verapamil (1:1) | PAA K752:HEC 250HX (1:1) | Simulated TP43 |
| TP83 | Verapamil (1:1) | PVME/MA S-97:PVP/VAc E-635 (1:1) | Simulated TP7 |
| SD58 | Verapamil (1:1) | PAA K752:HEC 250HX (1:1) | TP43 in capsules |
| TP87 | Verapamil (1:1) | PVME/MA S-97: PVP/VAc VA64 (1:1) | |
| TP88 | Verapamil (1:1) | PAA 934:HEC 250HHX (1:1) | |
| TP89 | Verapamil (1:1) | PVME/MA S-97:PVP/VAc VA64 (1:1) | |
| TP90 | Verapamil (1:1) | PAA 934:HEC 250HHX:PVP/VAc VA64 (1:1:1) | |
| TP91 | Verapamil (1:1) | PAA 934:PEO N10:PVA 107 (1:1:1) | |
| TP92 | Verapamil (1:1) | PAA 934:PEO N10:PVA 107 (1:1:1) | Same as TP91 |

TABLE 2-continued

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
|---|---|---|---|
| TP93 | Verapamil (1:1) | PAA 934:PEO N10:HEC 250HHX (1:1:1) | |
| TP96 | Verapamil (1:1) | PVME/MA S-97:PVP/VAc VA64:Gum Arabic (1:1:1) | |
| TP97 | Verapamil (1:1) | PAA K732:HEC 250HHX (1:1) | |
| TP98 | Verapamil (1:1) | PVA 107:PEO N10 (1:1) | |
| TP99 | Verapamil (1:1) | PAA K732:HEC 250HHX:PVP/VAc VA64 (1:1:1) | |
| TP100 | Verapamil (1:1) | PVME/MA S-97:PVP/VAc VA64:Gum Arabic (1:1:1) | Same as TP96, 35 cam |
| TP101 | Verapamil (1:1) | PAA 934:PVP/VAc VA64:PVA 107 (1:1:1) | |
| TP102 | Verapamil (1:1) | PAA 971 | |
| TP103 | Verapamil (1:1) | PVME/MA S-97:HEC 250HHX (1:1) | |
| TP104 | Verapamil (1:1) | HEC 250HHX | |
| TP105 | Verapamil (1:1) | PVME/MA S-97:PVP/VAc VA64:Gum Arabic (1:1:1) | Same as TP96, TP100 |
| TP106 | Verapamil (1:1) | PVME/MA S-97:HEC 250HHX (1:1) | |
| TP107 | Verapamil (1:1) | PAA 934:PEO N10:PVA 107 (1:1:1) | Same as TP91, TP92 |
| TP108 | Verapamil (1:1) | PAA 934:PVP/VAc VA64:HEC 250HHX (1:1:1) | |
| TP109 | Verapamil (1:1) | PVME/MA S-97:HPC 99LF (1:1) | |
| TP110 | Verapamil (1:1) | PVME/MA S-97:HEC 250 HX (1:1) | |
| TP111 | Verapamil (1:1) | PVME/MA AN119:PVP/VAc VA64:HEC 250HX (1:1:1) | |
| TP112 | Verapamil (1:1) | PAA 971:PVP/VAc VA64:PVA 107 (20:40:40) | |
| TP113 | Verapamil (1:1) | PVME/MA S-97:PVP/VAc VA64:Gum Arabic (1:1:1) | Same as TP96, TP100, TP105, 40 cam Oily - peanut oil 45 cam |
| TP114 | Verapamil (1:1) | PVME/MA S-97: PVP/VAc VA64:Gum Arabic (1:1:1) | Same as TP113, Post mixed |
| TP115 | Verapamil (1:1) | PVME/MA S-97: PVP/VAc VA64:HEC 250HHX (1:1:1) | |
| TP116 | Verapamil (1:1) | PVME/MA S-97: PVP/VAc VA64:HEC 250HHX (1:1:1) | Same as TP115, 40 cam |
| TP117 | Verapamil (1:1) | PVME/MA S-97: PVP/VAc VA64:Gum ARabic (1:1:1) | Same as TP96, TP100, TP113, TP114 30 cam, 500 mg tablets |
| TP118 | Verapamil (1:2) | PVME/MA S-97: PVP/VAc VA64:Gum Arabic (1:1:1) | |
| TP119 | Verapamil (1:1) | PVME/MA S-97: PVP/VAc VA64:Gum Arabic (1:1:1) | pH adjusted to 7.67 prior to spray drying |
| TP120 | Verapamil (1:1) | PAA 971:PVP/VAc VA64:Gum Arabic (1:1:1) | |
| TP121 | Verapamil (1:1) | PVME/MA S-97:PVP/VAc VA64:Gum Arabic (1:1:1) | 40 cam, 480 mg tablets |
| TP122 | Verapamil (1:1) | PVME/MA S-97:PVP/VAc VA64:HEC 250HHX (1:1:1) | 40 cam |
| TP123 | Verapamil (1:1) | PAA 907:PVP/VAc VA64:Gum Arabic (1:1:1) | |
| TP124 | Verapamil (1:1) | PAA 907:PVP/VAc VA64:HEC 250HX (1:1:1) | |
| TP125 | Verapamil (1:1) | PAA 971:PVP/VAc VA64:Gum Arabic (1:2:2) | |
| TP126 | Verapamil (1:1) | PVME/MA S-97:PVP/VAc VA64:HEC 250HX (1:1:1) | |
| TP127 | Verapamil (1:1) | PVME/MA S-97:PVP/VAc VA64:HPC 99LF (1:1:1) | |
| TP128 | Verapamil (1:1) | PAA 907:PVP/VAc VA64:Gum Arabic (1:1:1) | 40 cam |
| TP129 | Verapamil (1:1) | PVME/MA S-97:PVP/VAc VA64: (1:1) | |
| TP130 | Verapamil (1:1) | Sodium Alginate GMB:PVP/VAc VA64:Gum Arabic (1:1:1) | |
| TP131 | Verapamil (1:1) | PVME/MA S-97:PVP/VAc VA64:Gum Arabic (1:1:1) | pH of solution = 1 prior to spray drying |
| TP132 | Verapamil (1:1) | PVME/MA S-97:PVP/VAc VA64:HEC 250HX (2:2:1) | |
| TP133 | Verapamil (1:1) | PVME/MA S-97:PVP/VAc VA64:HEC 250M (1:1:1) | |
| TP134 | Verapamil (1:1) | PVME/MA S-97:PVP/VAc VA64:Gum Arabic (2:1:1) | |
| TP135 | Verapamil (1:1) | PAA 971:PVP/VAc VA64:Gum Arabic (10:45:45) | |
| TP136 | Verapamil (1:1) | PAA 907:PVP/VAc VA64:HEC 250HX (2:2:1) | |
| TP137 | Verapamil (1:1) | PVME/MA S-97:PVP/VAc VA64:Sodium Alginate GMB (1:1:1) | |
| TP138 | Verapamil (1:1) | PMMA/MA L100:PVP/VAc VA64:Gum Arabic (1:1:1) | |
| TP139 | Verapamil (1:1) | PAA 907:HEC 250HX (1:1) | |
| TP140 | Verapamil (1:1) | PAA 907:PVP/VAc VA64:HEC 250HX (45:45:10) | |
| TP141 | Verapamil (1:1) | PMMA/MA L100:PVP/VAc VA64 (1:1) | |
| TP142 | Verapamil (1:1) | PVME/MA S-97:PVP/VAc VA64:Gum Arabic (1:1:1) | System 1 (1st clinical trial) Same as TP121. TP105, TP96, TP100 |
| SD187 | Verapamil (1:1) | PVME/MA S-97:PVP/VAc VA64:Gum Arabic (1:1:1) | Spray-dried powder of TP142 in capsules |
| TP143 | Verapamil (1:1) | PVME/MA S-97:PVP/VAc VA64:Gum Arabic (1:2:2) | |
| TP144 | Verapamil (1:1) | PMMA/MA L100:PVP/VAc VA64:PVME/MA S-97 (1:2:1) | |
| TP145 | Diclofenac (1:1) | PVME/MA S-97:PVP/VAc VA64:Gum Arabic (1:1:1) | Protonated with 1 mol equivalent HCl |
| TP146 | Sodium Diclofenac (1:1) | PVME/MA S-97:PVP/VAc VA64:Gum Arabic (1:1:1) | |
| TP147 | Sodium Diclofenac (1:1) | PAA 907:PVP/VAc VA64:HEC 250HX (1:1:1) | |
| TP148 | Diclofenac (1:1) | PAA 907:PVP/VAc VA64:HEC 250HX (1:1:1) | Protonated with 1 mol equivalent HCl |
| TP149 | Diclofenac (1:1) | PVME/MA S-97:PVP/VAc VA64:HEC 250HX (2:2:1) | Protonated with 1 mol equivalent HCl |
| TP150 | Diclofenac (1:1) | PAA 907:PVP/VAc VA64:HEC 250HX (45:45:10) | Protonated with 1 mol equivalent HCl |
| TP151 | Diclofenac (1:1) | PVME/MA S-97:PVP/VAc VA64:HEC 250HX (30:40:30) | Protonated with 1 mol equivalent HCl |
| TP152 | Diclofenac (1:1) | PVME/MA S-97:PVP/VAc VA64:HPC 99LF (1:1:1) | Protonated with 1 mol equiavlent HCl |
| TP153 | Diclofenac (1:1) | PVME/MA S-97:PVP/VAc VA64:Gum Arabic (1:1:1) | Preprotonated |
| TP154 | Diclofenac (1:1) | PVME/MA S-97:PVP/VAc VA64:HPC 99LF (1:1:1) | Preprotonated |
| TP155 | Diclofenac (1:1) | PVME/MA S-97:HPC 99LF (1:1) | Preprotonated |
| TP156 | Diclofenac (1:1) | PVME/MA S-97:PVP/VAc VA64 (1:1) | Preprotonated |
| TP157 | Diclofenac (1:2) | PAA 907:HPC 99LF (1:1) | Preprotonated |
| TP158 | Diclofenac (1:2) | PAA 907:HPC 99LF (1:1) | Preprotonated |

TABLE 2-continued

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
|---|---|---|---|
| TP159 | Diclofenac (1:2) | PAA 907:PEO N10:HPC 99LF (1:1:1) | Preprotonated |
| TP160 | Diclofenac (1:2) | PAA 907:PVP/VAc VA64:HPC 99LF (1:1:1) | Preprotonated |
| TP161 | Diclofenac (1:1) | PVME/MA S-97:PEO N10:HEC 250HX (1:1:1) | Preprotonated |
| TP162 | Diclofenac (1:2) | PAA 907:PVP/VAc VA64:HPC 99EF (1:1:1) | Preprotonated |
| TP163 | Diclofenac (1:2) | PAA 971:PVP/VAc VA64:HPC 99EF (1:1:1) | Preprotonated |
| TP164 | Diclofenac (1:1) | PVME/MA S-97:PVP/VAc VA64:HEC 250HX (1:1:1) | Preprotonated |
| TP165 | Diclofenac (1:1) | PVME/MA S-97:PVP/VAc VA64:Sodium Alginate GMB (1:1:1) | Preprotonated |
| TP166 | Diclofenac (1:1) | PVME/MA S-97:PVP/VAc VA64:Gum Arabic (1:2:2) | Preprotonated |
| TP167 | Diclofenac (1:2) | PAA 971:PVP/VAc VA64:HPC 99EF (1:2:2) | Preprotonated |
| TP168 | Diclofenac (1:2) | PAA 971:PEO N10:HPC 99EF (1:2:2) | Preprotonated |
| TP169 | Diclofenac (1:1) | PVME/MA S-97:HPC 99EF (1:1) | Preprotonated |
| TP170 | Diclofenac (1:1) | PAA 97:PEO N10:HPC 99LF (1:2:2) | Preprotonated |
| TP171 | Diclofenac (1:1) | PVME/MA S-97:NaCMC (1:1) | Preprotonated |
| TP172 | Diclofenac (1:1) | PVME/MA S-97:PVP/VAc VA64:HPC 99LF (1:2:2) | Preprotonated |
| TP173 | Diclofenac (1:1) | PVME/MA S-97:PVP K30:HEC 250G (1:1:1) | Preprotonated |
| TP174 | Declofenac (1:1) | PAA 907:PVP K30:HPC 99EF (1:1:1) | |
| TP175 | Diclofenac (1:1) | PVME/MA S-97:PVP/VAc VA64:NaCMC (1:1:1) | Preprotonated |
| TP176 | Diclofenac (1:1) | PVME/MA AN139:PVP/VAc VA64 (1:1) | Preprotonated |
| TP177 | Diclofenac (1:1) | PVME/MA AN139:PVP/VAc VA64:HPC 99LF (1:1:1) | Preprotonated |
| TP178 | Diclofenac (1:1) | PVME/MA S-97:HPMC E15 (1:1) | Preprotonated |
| TP179 | Diclofenac (1:1) | PVME/MA S-97:PVP/VAc VA64:HPMC E5 (1:1:1) | Preprotonated |
| TP180 | Diclofenac (1:1) | PVME/MA S-97:PVP/VAc VA64 (34:66) | Preprotonated |
| TP181 | Diclofenac (1:1) | PVME/MA S-97:PVP/VAc VA64:PEO N10 (1:1:1) | Preprotonated |
| TP182 | Diclofenac (1:1) | PAA 971:HPC 99LF (1:1) | Preprotonated |
| TP183 | Verapamil (1:1) | PVME/MA S-97: PVP/VAc VA64:Gum Arabic (1:1:1) | Different cam pressure 30, 35, 40, 45 System 1 (1st clinical trial) Same as TP121, TP142 |
| TP184 | Diclofenac (1:1) | PVME/MA S-97:PVP/VAc VA64:HPC 99LF (1:2:2) | Preprotonated, 40 cam |
| TP185 | Diclofenac (1:1) | PAA 907:PVP/VAc VA64:HPC 99EF (1:1:2) | Preprotonated, 40 cam |
| TP186 | Diclofenac (1:1) | PVME/MA S-97:PVP/VAc VA64:PEO N10 (1:2:2) | Preprotonated, 40 cam |
| TP187 | Diclofenac (1:1) | PVME/MA AN139:PVP/VAc VA64:HPC 99LF (1:2:2) | Preprotonated, 40 cam |
| TP188 | Diclofenac (1:1) | PAA 907:PEO N10:HPMC E5 (1:2:2) | Preprotonated, 40 cam |
| TP189 | Diclofenac (1:1) | PVME/MA S-97:PVP/VAc VA64:PEO N10 (1:2:2) | Preprotonated |
| TP190 | Diclofenac (1:1) | PVME/MA S-97:PVP/VAc VA64:PEO N10 (1:1:1) | Preprotonated, 40 cam |
| TP191 | Diclofenac (1:1) | PAA 907:PEO N10:HPC 99LF (1:2:2) | Preprotonated |
| TP192 | Diclofenac (1:1) | PAA 907:PEO N10:HPMC E5 (1:2:2) | Preprotonated |
| TP193 | Diclofenac (1:1) | PVME/MA AN139:PVP/VAc VA64:HPC 99LF (1:2:2) | Preprotonated |
| TP194 | Diclofenac (1:1) | PAA 907:PVP/VAc VA64:HPC 99LF (1:2:2) | Preprotonated |
| TP195 | Diclofenac (1:1) | PAA 907:PVP/VAc VA64:HPC 99LF (1:1:1) | Protonated with 1 mol equivalent HCl |
| TP196 | Diclofenac (1:1) | PAA 907:PVP/VAc VA64:PEO N10 (1:1:1) | Preprotonated |
| TP197 | Diclofenac (1:1) | PVME/MA S-97:PVP/VAc VA64:PEO N10 (26:37:37) | Preprotonated |
| TP198 | Diclofenac (1:1) | PAA 907:PVP/VAc VA64:PEO N10 (26:37:37) | Preprotonated |
| TP199 | Diclofenac (1:1) | PVMe/MA S-97:PVP/VAc VA64:PEO N10 (30:35:35) | Preprotonated |
| TP200 | Diclofenac (1:1) | PVMe/MA S-97:PVP/VAc VA64:PEO N10 (1:1:1) | Preprotonated |
| TP201 | Diclofenac (1:1) | PAA 907:PVP/VAc VA64:HPC 99LF (30:35:35) | Preprotonated |
| TP202 | Diclofenac (1:1) | PMMA/MA L100:PVP/VAc VA64:HPC 99LF (1:1:1) | Preprotonated |
| TP203 | Diclofenac (1:1) | PVME/MA S-97:PVP/VAc VA64:HPC 99LF (1:2:2) | Preprotonated |
| TP204 | Diclofenac (1:1) | PAA 907:PEO N10:HPC 99LF (1:2:2) | Preprotonated |
| TP205 | Diclofenac (1:1) | PMMA/MA L100:PVP/VAc VA64:PEO N10 (1:1:1) | Preprotonated |
| TP206 | Diclofenac (1:1) | PAA 907:HPC 99LF (40:60) | Preprotonated |
| TP207 | Diclofenac (1:1) | PVME/MA S-97:PVP K30:HEC 250G (1:2:2) | Preprotonated |
| TP209 | Diclofenac (1:1) | PMMA/MA L100:PVP/VAc VA64:HPC 99LF (1:2:2) | Preprotonated |
| TP210 | Diclofenac (1:1) | PVME/MA S-97:PVP K30:HEC 250G (2:2:1) | Preprotonated |
| TP211 | Diclofenac (1:1) | PAA 971:PVP/VAc VA64:HPC 99LF (10:45:45) | Preprotonated |
| TP212 | Diclofenac (1:1) | PAA 971:HPC 99LF (30:70) | Preprotonated |
| TP213 | Diclofenac (1:1) | PAA 971:PVP/VAc VA64:PEO N10 (1:2:2) | Preprotonated |
| TP214 | Diclofenac (1:1) | PAA 971:HPMC E5 (30:70) | Preprotonated |
| TP215 | Diclofenac (1:1) | PMMA/MA L100:PVP/VAc VA64:PEO N10 (1:2:2) | Preprotonated |
| TP216 | Diclofenac (1:1) | PVME/MA S-97:PVP/VAc VA64:HPMC E5 (2:2:1) | Preprotonated |
| TP217 | Diclofenac (1:1) | PAA 971:PVP/VAc VA64:HPMC E5 (1:2:2) | Preprotonated |
| TP218 | Diclofenac (1:1) | PAA 971:HPMC E5 (4:96) | Preprotonated |
| TP219 | Diclofenac (1:1) | PMMA/MA L100:HPMC E5 (20:80) | Preprotonated |
| TP220 | Diclofenac (1:1) | PMMA/MA L100:HPC 99EF (20:80) | Preprotonated |
| TP221 | Diclofenac (1:1) | PAA 971:PEO N10:HPC 99EF (2:49:49) | Preprotonated |
| TP222 | Diclofenac (1:1) | PVME/MA S-97:PEO N10:HPC 99EF (1:2:1) | Preprotonated |
| TP223 | Diclofenac (1:1) | PAA 907:HPC 99EF (40:60) | Preprotonated |
| TP224 | Verapamil (1:1) | PVME/MA S-97:PVP/VAc VA64:GumArabic (1:1:1) | 5 × 100 mg tablets, 35 cam each |
| TP225 | Verapamil (1:1) | PVME/MA S-97:PVP/VAc VA64:GumArabic (1:1:1) | 12.5 mm tablets, 40 cam |
| TP226 | Sodium Diclofenac | PVME/MA S-97:PVP/VAc VA64:Gum Arabic (1:1:1) | Post mixed, 40 cam |
| TP227 | Verapamil (1:1) | PVME/MA S-97:PVP/VAc VA64:Gum Arabic (1:2:2) | 12.5 mm tablets, 40 cam |
| TP228 | Verapamil (1:1) | PVME/MA S-97:PVP/VAc VA64:Gum Arabic (30:35:35) | 12.5 mm tablets, 40 cam |
| TP229 | Verapamil (1:1) | PVME/MA S-97:PVP/VAc VA64:Gum Arabic (1:2:1) | 12.5 mm tablets, 40 cam |

TABLE 2-continued

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
|---|---|---|---|
| TP230 | Verapamil (2:1) | PVME/MA S-97:PVP/VAc VA64:Gum Arabic (1:1:1) | 40 cam |
| TP231 | Verapamil (1:1) | PVME/MA S-97:PVP/VAc VA64:Gum Arabic (10:45:45) | 12.5 mm tablets, 40 cam |
| TP232 | Verapamil (1:1) | PVME/MA S-97:PVP/VAc VA64 (30:70) | 12.5 mm tablets, 40 cam |
| TP233 | Verapamil (1:1) | PVP/VAc VA64:Gum Arabic (1:1) | 12.5 mm tablets, 40 cam |
| TP234 | Verapamil (1:1) | PVME/MA S-97:Gum Arabic (1:1) | 12.5 mm tablets, 40 cam |
| TP235 | Verapamil (1:1) | PVME/MA S-97:PVP/VAc VA64:Gum Arabic (5:47.5:47.5) | 12.5 mm tablets, 40 cam |
| TP236 | Verapamil (1:1) | PVME/MA S-97:PVP/VAc VA64:Gum Arabic (2:49:49) | 12.5 mm tablets, 40 cam |
| TP237 | Verapamil (1:1) | PVME/MA S-97:PVP/VAc VA64 (90:10) | 12.5 mm tablets, 40 cam |
| TP238 | Verapamil (1:1) | PVME/MA S-97:PVP/VAc VA64 (10:90) | 12.5 mm tablets, 40 cam |
| TP239 | Verapamil (1:1) | PVME/MA S-97:PVP/VAc VA64:Gum Arabic (2:1:2) | 12.5 mm tablets, 10% sodium starch glycolate post mixed, 40 cam |
| TP240 | Verapamil (1:1) | PVME/MA S-97:PVP/VAc VA64 (70:30) | 12.5 mm tablets, 10% sodium starch glycolate post mixed, 40 cam |
| TP241 | Verapamil (1:1) | PVME/MA S-97:PVP/VAc VA64:Gum Arabic (1:1:2) | 12.5 mm tablets, 10% sodium starch glycolate post mixed, 40 cam |
| TP242 | Verapamil (1:1) | PVME/MA S-97:PVP/VAc VA64:Gum Arabic (15:15:70) | 12.5 mm tablets, 10% sodium starch glycolate post mixed, 40 cam |
| TP243 | Verapamil (1:1) | PVME/MA S-97:PVP/VAc VA64:HPC 99EF (1:2:2) | 12.5 mm tablets, 10% sodium starch glycolate post mixed, 40 cam |
| TP244 | Verapamil (1:1) | PVME/MA S-97:HPC 99EF (30:70) | 12.5 mm tablets, 10% sodium starch glycolate post mixed, 40 cam |
| TP245 | Verapamil (1:1) | PVME/MA S-97:PVP/VAc VA64:Gum Arabic (1:1:1) | 12.5 mm tablets, 10% sodium starch glycolate post mixed, 40 cam |
| TP246 | Verapamil (1:1) | PVME/MA S-97:PVP/VAc VA64:Sodium Alginate GMB (1:1:1) | 12.5 mm tablet, 40 cam |
| TP247 | Verapamil (1:1) | PAA 907:HPC 99EF (10:90) | 12.5 mm tablets, 40 cam |
| TP248 | Verapamil (1:1) | PVME/MA S-97:PVP/VAc VA64:Gum Arabic (1:1:1) | 12.5 mm tablets, 1 mol equivalent HCl added prior to spray drying, 40 cam |
| TP249 | Verapamil (1:1) | PVME/MA S-97:PVP/VAc VA64:Gum Arabic (1:1:1) | 12.5 mm tablets, 1 mol equivalent NaCO$_3$ added prior to spray drying, 40 cam |
| TP250 | Verapamil (1:1) | PVME/MA S-97:PVP/VAc VA64:PEO N10 (1:1:1) | 12.5 mm tablets, 40 cam |
| TP251 | Verapamil (1:1) | PVME/MA S-97:PVP/VAc VA64:HPMC E5 (1:1:1) | 12.5 mm tablets, 40 cam |
| TP252 | Verapamil (1:1) | Sodium Alginate GMB:PVP/VAc VA64:HPMC E5 (1:1:1) | 12.5 mm tablets, 40 cam |
| TP253 | Verapamil (1:1) | PVME/MA S-97:PVP/VAc VA64:HEC 250 HX (2:2:1) | 12.5 mm tablets, 40 cam |
| TP254 | Verapamil (1:1) | PAA 907:Sodium Alginate GMB:HPC 99EF (10:30:60) | 12.5 mm tablets, 40 cam |
| TP255 | Verapamil (1:1) | PAA 907:HPMC E5:Dextrin (13:53:33) | 12.5 mm tablets, 40 cam |
| TP256 | Verapamil (1:1) | PAA 907:HPC 99EF:Sucrose (13:53:33) | 12.5 mm tablets, 40 cam |
| TP257 | Verapamil (1:1) | PVME/MA S-97:PVP/VAc VA64:Gum Arabic (10:30:60) | 12.5 mm tablets, 40 cam |
| TP258 | Verapamil (1:1) | PAA 907:Sodium Alginate GMB:HPMC E5 (10:10:80) | 12.5 mm tablets, 40 cam |
| TP259 | Verapamil (1:1) | Sodium Alginate LF10/60:PVP/VAc VA64:HPMC E5 (1:1:1) | 12.5 mm tablets, 40 cam |
| TP260 | Verapamil (1:1) | PAA 907:HPC 99EF (10:90) | 12.5 mm tablets, 1% aerosil added prior to spray drying, 40 cam |
| TP261 | Verapamil (1:1) | PAA 907:HPMC E5 (10:90) | 12.5 mm tablets, 40 cam |
| TP262 | Verapamil (1:1) | PAA 907:Sodium Alginate LF10/60:HPC 99EF (10:10:80) | 12.5 mm tablets, 40 cam |
| TP263 | Diclofenac (1:1) | PVME/MA S-97:PVP/VAc VA64:HPMC E5 (10:45:45) | Preprotonated, 8 mm tablets, 40 cam |
| TP264 | Diclofenac (1:1) | PAA 907:PVP/VAc VA64:HPC 99EF (10:45:45) | Preprotonated, 8 mm tablets, 40 cam |
| TP266 | Diclofenac (1:1) | PVME/MA S-97:PVP/VAc VA64:PEO N10 (10:60:30) | Preprotonated, 8 mm tablets, 40 cam |
| TP267 | Verapamil (1:1) | Sodium Alginate LF10/60:PVP/VAc VA64:HPMC E5 (1:1:1) | System 2 (2nd clinical trail) 12.5 mm tablets, 40 cam, same as TP259 |
| TP268 | Diclofenac (1:1) | PAA 907:HPC 99EF:Lactose (10:70:20) | Preprotonated, 8 mm tablets, 40 cam |
| TP269 | Diclofenac (1:1) | Sodium Alginate LF10/60:PVP/VAc VA64:HPMC E5 (1:1:1) | Preprotonated, 8 mm tablets, 40 cam |
| TP270 | Diclofenac (1:1) | PAA 907:PVP/VAc VA64:HPC 99EF (20:20:60) | Preprotonated, 8 mm tablets, 40 cam |
| TP271 | Diclofenac (1:1) | PAA 907:HPC 99EF:Lactose (10:70:20) | Preprotonated, 8 mm tablets, 10% sodium starch glycolate post mixed, 40 cam |
| TP272 | Verapamil (1:1) | PAA 907:HPMC E5 (10:90) | 12.5 mm tablets, 40 cam |
| TP273 | Diclofenac (60:40) | Sodium Alginate LF10/60:PVP/VAc VA64:HPMC E5 (1:1:1) | Preprotonated, 8 mm tablets, 40 cam |
| TP274 | Verapamil (70:30) | PAA 907:HPMC E5 (10:90) | 12.5 mm tablets, 40 cam |
| TP275 | Verapamil (60:40) | PAA 907:HPMC E5 (10:90) | 12.5 mm tablets, 40 cam |
| TP276 | Verapamil (1:1) | PMMA/MA L100:HPMC E5 (10:90) | 12.5 mm tablets, 40 cam |
| TP277 | Verapamil (1:1) | PMMA/MA L100:HPC 99EF (10:90) | 12.5 mm tablets, 40 cam |
| TP278 | Verapamil (1:1) | PMMA/MA L100:PVP/VAc VA 64 (10:90) | 12.5 mm tablets, 40 cam |
| TP279 | Verapamil (60:40) | PMMA/MA L100:HPMC E5 (5:95) | 12.5 mm tablets, 40 cam |
| TP280 | Verapamil (60:40) | PMMA/MA L100:HPMC E5 (10:90) | 12.5 mm tablets, 40 cam |
| TP281 | Verapamil (1:1) | PMMA/MA L100:PVP/VAc VA64:HPMC E5 (1:1:1) | 12.5 mm tablets, 40 cam |
| TP282 | Diclofenac (1:1) | Sodium Alginate LF10/60:PVP/VAc VA64:HPMC E5 (1:1:1) | System 1 (2nd clinical trail), preprotonated, 40 cam, same as TP273 |
| TP283 | Verapamil (60:40) | PMMA/MA L100:HPMC E5 (10:90) | System 3 (2nd clinical trail) 12.5 mm tablets, 40 cam, same as TP280 |
| TP284 | Vearpamil (1:1) | HPMC E5 | 12.5 mm tablets, 40 cam, 2% aerosil post mixed |

TABLE 2-continued

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
| --- | --- | --- | --- |
| TP285 | Verapamil (1:1) | Sodium Alginate LF10/60 | 12.5 mm tablets, 40 cam, 2% aerosil post mixed |
| TP286 | Verapamil (1:1) | PVP/VAc VA64 | 12.5 mm tablets, 40 cam, 2% aerosil post mixed |
| TP287 | Verapamil (1:1) | PAA 971:HPMC E5 (1:9) | 12.5 mm tablets, 40 cam, 2% aerosil post mixed |
| TP288 | Verapamil (1:1) | PAA 971:HPC 99EF (1:9) | 12.5 mm tablets, 40 cam, 2% aerosil post mixed |
| TP289 | Diclofenac (1:1) | PMMA/MA L100:HPMC E5 (10:90) | Preprotonated, 8 mm tablets, 40 cam, 2% aerosil post mixed |
| TP290 | Diclofenac (1:1) | PAA 971:HPC 99EF (1:9) | Preprotonated, 8 mm tablets, 40 cam, 2% aerosil post mixed |
| TP291 | Verapamil (1:1) | PAA 971:Gum Arabic (1:9) | 12.5 mm tablets, 40 cam, 2% aerosil post mixed |
| TP292 | Verapamil (1:1) | PAA 971:HPC 99EF:Lactose (5:45:50) | 12.5 mm tablets, 40 cam, 2% aerosil post mixed |
| TP293 | Diclofenac (1:1) | PMMA/MA L100:HPMC E5 (10:90) | Preprotonated, 8 mm tablets, 40 cam, 2% aerosil and 10% sodium starch glycolate post mixed |
| TP294 | Diclofenac (1:1) | PAA 971:HPC 99EF (1:9) | Preprotonated, 8 mm tablets, 40 cam, 2% aerosil and 10% sodium starch glycolate post mixed |
| TP295 | Verapamil (1:1) | PMMA/MA L100:Gum Arabic (1:9) | 12.5 mm tablet, 40 cam, 2% aerosil post mixed |
| TP296 | Verapamil (1:1) | PAA 971:HPMC E15 (1:9) | 12.5 mm tablets, 40 cam, 2% aerosil post mixed |
| TP297 | Verapamil (1:1) | PAA 971:HPC 99EF (2:98) | 12.5 mm tablets, 40 cam, 2% aerosil post mixed |
| TP298 | Verapamil (1:1) | PAA 971:Gum Arabic (1:9) | 12.5 mm tablets, 40 cam, 2% aerosil and 10% sodium starch glycolate post mixed |
| TP299 | Verapamil (1:1) | PAA 971:Gum Arabic (5:95) | 12.5 mm tablets, 40 cam, 2% aerosil post mixed |
| TP300 | Verapamil (1:1) | PAA 971:PVP/VAc VA64:HPC 99EF (5:75:20) | 12.5 mm tablets, 40 cam, 2% aerosil post mixed |
| TP301 | Diclofenac (1:1) | PAA 971:PVP/VAc VA64:HPC 99EF (5:50:45) | Preprotonated, 8 mm tablets, 40 cam, 2% aerosil post mixed |
| TP302 | Diclofenac (1:1) | PMMA/MA L100:PVP/VAc VA64:HPMC E5 (2:68:30) | Preprotonated, 8 mm tablets, 40 cam, 2% aerosil post mixed |
| TP303 | Verapamil (1:1) | Gum Arabic | 12.5 mm tablets, 40 cam, 2% aerosil post mixed |
| TP304 | Verapamil (1:1) | PAA 907 | 12.5 mm tablets, 40 cam, 2% aerosil post mixed |
| TP305 | Verapamil (1:1) | PAA 907:Gum Arabic (1:1) | 12.5 mm tablets, 40 cam, 2% aerosil post mixed |
| TP306 | Verapamil (1:1) | PAA 971:Gum Arabic (2:98) | 12.5 mm tablets, 40 cam, 2% aerosil post mixed |
| TP307 | Verapamil (1:1) | PAA 971:Lactose (5:95) | 12.5 mm tablets, 40 cam, 2% aerosil post mixed |
| TP308 | Verapamil (1:1) | PMMA/MA L100:Gum Arabic (5:95) | 12.5 mm tablets, 40 cam, 2% aerosil post mixed |
| TP309 | Verapamil (1:1) | PAA 971:Tartaric acid (1:1) | 12.5 mm tablets, 40 cam, 2% aerosil post mixed |
| TP310 | Verapamil (4:6) | PMMA/MA L100:HPMC E5 (10:90) | 12.5 mm tablets, 40 cam |
| TP311 | Verapamil (1:1) | PMMA/MA L100:HPMC E5 (10:90) | 12.5 mm tablets, 40 cam, 2% aerosil post mixed |
| TP312 | Verapamil (1:1) | PMMA/MA L100:HPMC E5 (10:90) | 12.5 mm tablets, 40 cam, 2% aerosil post mixed |
| TP313 | Verapamil (1:1) | PMMA/MA L100-55:HPMC E5 (10:90) | 12.5 mm tablets, 40 cam, 2% aerosil post mixed |
| TP314 | Verapamil (1:1) | PMMA/MA L100:HPMC E5 (10:90) | 12.5 mm tablets, 40 cam, 2% aerosil post mixed |
| TP315 | Diclofenac (1:1) | PMMA/MA L100:HPMC E5 (10:90) | Preprotonated, 8 mm tablets, 40 cam, 2% aerosil post mixed |
| TP316 | Diclofenac (1:1) | PMMA/MA L100:PVP/VAc VA64:HPMC E5 (5:65:30) | Preprotonated, 8 mm tablets, 40 cam, 2% aerosil post mixed |
| TP317 | Diclofenac (1:1) | PMMA/MA L100:HPMC E5 (10:90) | Preprotonated, 8 mm tablets, 40 cam, 2% aerosil and 1% sodium starch glycolate post mixed |
| TP318 | Diclofenac (1:1) | PAA 971:Gum Arabic (2:98) | Preprotonated, 8 mm tablets, 2% aerosil post mixed |

TABLE 2-continued

Experimental interpolymer complexation systems (All the systems contain 1.5% magnesium stearate as a die lubricating agent. All the tablets are compressed to 45 cam except if indicated otherwise.) Tablet size 10 mm unless specified.

| System reference | Drug (drug:polymer ratio excluding Mg stearate) | Polymer Composition | Additional parameters |
|---|---|---|---|
| TP319 | Sodium Diclofenac (1:1) | PAA 971:Gum Arabic (10:90) | 8 mm tablets, 40 cam, 2% aerosil post mixed |
| TP320 | Sodium Diclofenac (1:1) | PAA 971:HPMC E5 (10:90) | 8 mm tablets, 40 cam, 2% aerosil post mixed |
| TP321 | Sodium Diclofenac (1:1) | PAA 971:PVP/VAc VA64:HPMC E5 (5:65:30) | 8 mm tablets, 40 cam, 2% aerosil post mixed |
| TP322 | Sodium Diclofenac (1:1) | PAA 971:PVP/VAc VA64:HPMC E5 (10:60:30) | 8 mm tablets, 40 cam, 2% aerosil post mixed |
| TP323 | Sodium Diclofenac (1:1) | PAA 971:HPMC E5 (5:95) | 8 mm tablets, 40 cam, 2% aerosil post mixed |
| TP324 | Sodium Diclofenac (1:1) | PAA 971:Gum Arabic (40:60) | 8 mm tablets, 45 cam, 2% aerosil post mixed |
| TP325 | Diclofenac (1:1) | PMMA/MA L100:HPMC E5 (5:95) | Preprotonated, 8 mm tablets, 40 cam, 2% aerosil post mixed |
| TP326 | Sodium Diclofenac (1:1) | PAA 971:PVP/VAc VA64:Gum Arabic (2:49:49) | 8 mm tablets, 40 cam, 2% aerosil post mixed |
| TP327 | Sodium Diclofenac (1:1) | PAA 971:HPMC E5:Gum Arabic (5:30:65) | 8 mm tablets, 40 cam, 2% aerosil post mixed |
| TP328 | Sodium Diclofenac (1:1) | PMMA/MA L100:HPMC E5 (1:9) | 8 mm tablets, 40 cam, 2% aerosil post mixed |
| TP329 | Sodium Diclofenac (1:1) | PMMA/MA L100:HPMC E5 (2:8) | 8 mm tablets, 40 cam, 2% aerosil post mixed |
| TP330 | Sodium Diclofenac (1:1) | PMMA/MA L100:HPMC E5 (1:1) | 8 mm tablets, 40 cam, 2% aerosil post mixed |
| TP331 | Diclofenac (1:1) | PAA 971:HPMC E5:Lactose (5:45:50) | Preprotonated, 8 mm tablets, 40 cam, 2% aerosil post mixed |
| TP332 | Diclofenac (1:1) | PAA 971:PEO N10:Lactose (5:45:50) | Preprotonated, 8 mm tablets, 40 cam, 2% aerosil post mixed |
| TP333 | Diclofenac (1:1) | PAA 971:PVP/VAc VA64:HPMC E5 (2:65:33) | Preprotonated, 8 mm tablets, 40 cam, 2% aerosil post mixed |
| TP334 | Diclofenac (1:1) | PAA 971:PVP/VAc VA64: HPMC E5 (10:45:45) | Preprotonated, 8 mm tablets, 40 cam, 2% aerosil post mixed |
| TP335 | Diclofenac (1:1) | PAA 971:PVP/VAc VA64:HPMC E5 (6:47:47) | Preprotonated, 8 mm tablets, 40 cam, 2% aerosil post mixed |
| TP336 | Diclofenac (1:1) | PMMA/MA L100:HPC 99LF (1:9) | Preprotonated, 8 mm tablets, 40 cam, 2% aerosil post mixed |
| TP337 | Diclofenac (1:1) | PMMA/MA L100:HPMC E5 (5:95) | Preprotonated, 8 mm tablets, 40 cam, 2% aerosil post mixed |
| TP338 | Diclofenac (1:1) | PAA AA1:HPMC E5 (1:9) | Preprotonated, 8 mm tablets, 40 cam, 2% aerosil post mixed |
| TP339 | Diclofenac (4:6) | PMMA/MA L100:HPMC E5 (1:9) | Preprotonated, 8 mm tablets, 40 cam, 2% aerosil post mixed |
| TP340 | Diclofenac (1:1) | PMMA/MA L100-55: HPMC E5 (1:9) | Preprotonated, 8 mm tablets, 40 cam, 2% aerosil post mixed |
| TP341 | Diclofenac (1:1) | PMMA/MA L100-55: PVP/VAc VA64:HPMC E5 (10:45:45) | Preprotonated, 8 mm tablets, 40 cam, 2% aerosil post mixed |
| TP342 | Diclofenac (1:1) | PAA AA1:PVP/VAc VA64:HPMC E5 (5:47.5:47.5) | Preprotonated, 8 mm tablets, 40 cam, 2% aerosil post mixed |
| TP343 | Diclofenac (1:1) | PMMA/MA L100-55: PVP/VAc VA64:HPMC E5 (1:1:1) | Preprotonated, 8 mm tablets, 40 cam, 2% aerosil post mixed |
| TP344 | Diclofenac (1:1) | PMMA/MA L100:PVP/VAc VA64:HPMC E5 (10:60:30) | Preprotonated, 8 mm tablets, 40 cam, 2% aerosil post mixed |
| TP345 | Diclofenac (1:1) | PMMA/MA L100-55:PVP/VAc VA64:HPMC E5 (10:45:45) | Preprotonated, 8 mm tablets, 40 cam, 2% aerosil post mixed |
| TP346 | Diclofenac (1:1) | PMMA/MA L100:HPMC E5 (1:9) | Preprotonated, 8 mm tablets, 40 cam, 2% aerosil post mixed |
| TP347 | Diclofenac (1:1) | PMMA/MA L100-55:PVP/VAc VA64:HPMC E5 (1:1:1) | Preprotonated, 8 mm tablets, 40 cam, 2% aerosil post mixed |

Key:
HEC Hydroxyethylcellulose
HPC Hydroxypropylcellulose
HPMC Hydroxypropylmethylcellulose
PAA Poly(acrylic acid)
PEO Poly(ethylene oxide)
PMMA/MA Methyl methacrylate/Methacrylic acid copolymer
PVA Poly(vinyl alcohol)
PVAc Poly(vinyl acetate)
PVME/MA Vinyl methyl ether/Maleic acid copolymer
PVP Poly(vinyl pyrrolidone)
PVP/VAc Vinyl pyrrolidone/vinyl acetate copolymer

What is claimed is:

1. A method of making a solid interpolymer complex for use as a controlled release matrix for a controlled release product for oral administration, from a first polymer and one or more second complementary polymers capable of complexing with the first polymer to form the interpolymer complex, wherein one of the first polymer or the second complementary polymer is a synthetic polymer, which method includes the steps of:

(1) dissolving the first polymer in a solvent;

(2) dissolving the second complementary polymer in a solvent therefor, the solvent for said second polymer being the same as that used for step (1) or different;

(3) the solvent in at least one of step (1) or (2) functioning as a complexation inhibitor or adding a complexation inhibitor to the solution of step (1) or the solution of step (2), so that a complexation inhibitor is present to prevent the interpolymer complex from precipitating from solution prior to step (6);

(4) mixing together the solutions of steps (1) and (2);

(5) if necessary, adjusting the pH of the mixture of step (4) to insure the desired complexation when solvent is removed while avoiding precipitation of the complex; and (6) spraying the resulting solution into a vessel to remove solvent, including any complexation inhibitor added thereto, to enable the polymers to complex and thereby produce solid particles of said complex.

2. A method according to claim 1 wherein the first polymer and the second complementary polymer are selected from the group consisting of alginates; alkyl and hydroxyalkylcelluloses; carboxymethylcellulose and its salts; carrageenan; cellulose and its derivatives; guar gum; gum arabic; vinyl methyl ether/maleic anhydride copolymers; pectins; poly(acrylamide); poly(acrylic acid) and its salts; poly(ethylene glycol); poly(ethylene imine); poly(ethylene oxide); poly(methacrylic acid); poly(vinyl acetate); poly(vinyl alcohol); poly(vinyl amine); poly(vinyl) pyrrolidone); poly(vinyl sulphonic acid); starches and their derivatives; styrene/maleic anhydride copolymers; xanthan gum; and their co-polymers.

3. A method according to claim 1 wherein the solvent in step (1) and the solvent in step (2) are selected from the group consisting of water, an alcohol, acetone and mixtures thereof.

4. A method according to claim 1 wherein the complexation inhibitor is selected from the group consisting of acetic acid, an alcohol, acetone, DMSO, glycerine and mixtures thereof.

5. A method according to claim 1 wherein in step (6) the spraying is spray drying.

6. A process of making a controlled release product for oral administration from an interpolymer complex and an active agent, wherein the interpolymer complex is made from a first polymer and a second complementary polymers capable of complexing with the first polymer to form the interpolymer complex, wherein one of the first polymer or the second complementary polymer is a synthetic polymer, which method includes the steps of:

(1) dissolving the first polymer in a solvent;

(2) dissolving the second complementary polymer in a solvent therefor, the solvent for said second polymer being the same as that used for step (1) or different;

(3) the solvent in at least one of step (1) or (2) functioning as a complexation inhibitor or adding a complexation inhibitor to the solution of step (1) or the solution of step (2), so that a complexation inhibitor is present to prevent the interpolymer complex from precipitating from solution prior to step (6);

(4) mixing together the solutions of steps (1) and (2);

(5) if necessary, adjusting the pH of the mixture of step (4) to insure the desired complexation when solvent is removed while avoiding precipitation of the complex;

(6) spraying the resulting solution into a vessel to remove solvent, including any complexation inhibitor added thereto, to enable the polymers to complex and thereby produce solid particles of said complex; and (7) incorporating the active agent into said interpolymer complex to form the controlled release product.

7. The process of claim 6 which comprises providing the active agent in the form of a dry powder or as a solution, dispersion, emulsion or slurry thereof in a liquid medium and adding the same to the solution of polymer of step (1) or (2) before step (4).

8. The process of claim 6 which comprises providing the active agent in the form of a dry powder or as a solution, dispersion, emulsion or slurry thereof in a liquid medium and adding the same to the mixture of step (4) before the spraying step (6).

9. The process of claim 6 wherein the active agent is fluidized in the vessel into which the solution is sprayed in step (6) to thereby encapsulate the active agent in a coating of the interpolymer complex.

10. A process according to claim 6 wherein in step (g) the active agent in solid or liquid form is mixed with the interpolymer complex, and the product is compressed to produce a tablet or a mini tablet.

11. A process according to claim 6 wherein the first polymer and the second complementary polymer are selected from the group consisting of alginates; alkyl and hydroxyalkylcelluloses; carboxymethylcellulose and its salts; carrageenan; cellulose and its derivatives; guar gum; gum arabic; vinyl methyl ether/maleic anhydride copolymers; pectins; poly(acrylamide); poly(acrylic acid) and its salts; poly(ethylene glycol); poly(ethylene imine); poly(ethylene oxide); poly(methacrylic acid); poly(vinyl acetate); poly(vinyl alcohol); poly(vinyl amine); poly(vinyl) pyrrolidone); poly(vinyl sulphonic acid); starches and their derivatives; styrene/maleic anhydride copolymers; xanthan gum; and their copolymers and the like.

12. A process according to claim 6 wherein the solvent in step (a) and the solvent in step (b) are selected from the group consisting of water, an alcohol, acetone and mixtures thereof.

13. A process according to claim 6 wherein the complexation inhibitor is selected from the group consisting of acetic acid, an alcohol, acetone, DMSO, glycerine and mixtures thereof.

14. A process according to claim 6 wherein in step (f) the spraying is spray drying.

15. A process according to claim 6 wherein the active agent is selected from the group consisting of verapamil, diltiazem, indomethacin diclofenac, isosorbide-5-mononitrate, zidovudine, pentoxiphylline, levodopa/carbidopa and cisapride.

* * * * *